(12) United States Patent
Vicente et al.

(10) Patent No.: US 8,071,760 B2
(45) Date of Patent: Dec. 6, 2011

(54) BORON-CONTAINING PORPHYRIN COMPOUNDS AND THEIR USES

(75) Inventors: Maria da Graça Henriques Vicente, Baton Rouge, LA (US); Erhong Hao, Anhui (CN)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 413 days.

(21) Appl. No.: 12/091,211

(22) PCT Filed: Oct. 25, 2006

(86) PCT No.: PCT/US2006/041396
§ 371 (c)(1),
(2), (4) Date: Oct. 28, 2008

(87) PCT Pub. No.: WO2007/050564
PCT Pub. Date: May 3, 2007

(65) Prior Publication Data
US 2009/0318680 A1    Dec. 24, 2009

Related U.S. Application Data

(60) Provisional application No. 60/730,331, filed on Oct. 25, 2005.

(51) Int. Cl.
*C07B 47/00* (2006.01)
*C07D 487/22* (2006.01)

(52) U.S. Cl. ........................................ 540/145
(58) Field of Classification Search ................... 540/145
See application file for complete search history.

(56) References Cited

U.S. PATENT DOCUMENTS 4,959,356 A * 9/1990 Miura et al. ................ 424/1.81
2005/0124596 A1 * 6/2005 Zhang et al. ................ 514/176

FOREIGN PATENT DOCUMENTS

WO    WO 01/85736    11/2001

OTHER PUBLICATIONS

Barth, R. et al., "Boron Neutron Capture Therapy of Cancer: Current Status and Future Prospects," *Clin. Canc. Res.*, vol. 11, No. 11, pp. 3987-4002 (2005).
Barth, R., "Boron Neutron Capture Therapy for Cancer," *Cancer*, vol. 70, pp. 2995-3007 (1992).
Barth, R. F. et al., "Boron Neutron Capture Therapy of Brain Tumors: An Emerging Therapeutic Modality," *Neurosurg.*, vol. 44, No. 3, pp. 433-451 (1999).
Bobadova-Parvanova, P. et al., "*Ab initio* and $^1$H-NMR Study of the Zn(II) Complexes of a *nido*- and a *closo*-Carboranylporphyrin," *Journal of Porphyrins and Phthalocyanines*, vol. 8, pp. 996-1006 (2004).
Bonnett, R., "Photosensitizers of the Porphyrin and Phthalocyanine Series for Photodynamic Therapy," *Chem. Soc. Rev.*, vol. 24, pp. 19-33 (1995).
Chayer, S. et al., "Syntheses of Carboranylpyrroles," *Tetrahedron Letters*, vol. 42, pp. 7759-7761 (2001).
Clark, J. C. et al., "Novel Carboranylporphyrins for Application in Boron Neutron Capture Therapy (BNCT) of Tumors," *Tetrahedron Letters*, vol. 46, pp. 2365-2368 (2005).
Clark, J. C. et al., Syntheses and Properties of Carboranylpyrroles. *Journal of Porphyrins and Phthalocyanines*, vol. 9, 803-810 (2005).
Dougherty, T. J. et al., "Photodynamic Therapy," *Natl. Cancer Inst.*, 1998, vol. 90, 889-905 (1998).
Elowitz, E. H. et al., "Biodistribution of *p*-Boronophenylalanine in Patients with Glioblastoma Multiforme for Use in Boron Neutron Capture Therapy," *Neurosurgery*, vol. 42, No. 3, pp. 463-469. (1998).
Fabre, B. et al., "First conducting Polymer Functionalized with Covalently Linked Carborane Units," *Electrochemistry Communications*, vol. 5, pp. 431-434 (2003).
Fabre, B. et al., Synthesis and Electrochemistry of Carboranylpyrroles. Toward the Preparation of Electrochemically and Thermally Resistant Conjugated Polymers. *Macromolecules*, vol. 39. pp. 112-119 (2006).
Gottumukkala, V. et al., "Synthesis and Cellular Studies of an Octa-anionic 5,10,15,20-Tetra[3,5-(*nido*-carboranylmethyl)phenyl]porphyrin (H2OCP) for Application in BNCT," *Bioorganic and Medicinal Chemistry*, vol. 13, pp. 1633-1640 (2005).
Gottumukkala, V. et al., "Synthesis, Cellular Uptake and Animal Toxicity of a Tetra(carboranylphenyl)-tetrabenzoporphyrin," *Biorganic and Medicinal Chemistry*, vol. 14, pp. 1871-1879 (2006).
Hao, E. et al., "Expeditious Synthesis of Porphyrin-cobaltacarborane Conjugates," *Chemical Communications*, pp. 1306-1308 (2005).
Hao, E. et al., "Synthesis of Oxacalixarene-Locked Bisporphyrins and Higher Oligomers," *Journal of Organic Chemistry*, vol. 71, 1233-1236 (2006).

(Continued)

*Primary Examiner* — Paul V. Ward
(74) *Attorney, Agent, or Firm* — John H. Runnels; Bonnie J. Davis

(57) ABSTRACT

Boron-containing porphyrin compounds are disclosed that may be used for boron neutron capture therapy of tumors, radiotherapy of tumors, and photodynamic therapy of tumors.

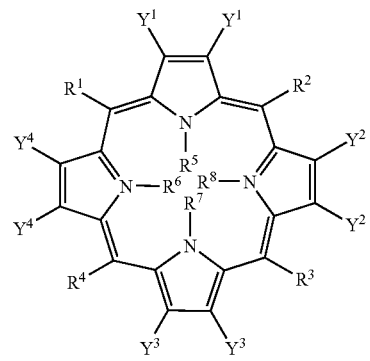

14 Claims, 20 Drawing Sheets

OTHER PUBLICATIONS

Hao, E. et al., "Synthesis and Cellular Studies of Porphyrin-Cobaltacarborane Conjugates," *Bioconjugate Chemistry*, vol. 16, 1495-1502 (2005).

Hawthorne, M. F., "New Horizons for Therapy Based on the Boron Neutron Capture Reaction," *Mol. Med. Today*, vol. 4, pp. 174-181 (199, (1994).

Hawthorne, M. F. "The Role of Chemistry in the Development of Boron Neutron Capture Therapy of Cancer," *Angew. Chem. Int. Ed. Engl.*, vol. 32, 950-984 (1993).

Kageji, T. et al., "Pharmacokinetics and Boron Uptake of BSH ($Na_2B_{12}H_{11}SH$) in Patients With Intracranial Tumors," *Neurooncol.*, vol. 33, pp. 117-130 (1997).

Kawabata, S. et al., "Evaluation of Carboranylporphyrins as Potential Delivery Agents for Neutron Capture Therapy of Brain Tumors," Proc Amer Assoc Cancer Res, vol. 46, p. 4754 (2005).

Kawabata, S. et al., "Evaluation of Carboranylporphyrins as Boron Delivery Agents for Neutron Capture Therapy," *Proceedings for the 12th International Symposium on Neutron Capture Therapy for Cancer*, pp. 123-126 (2006).

Kawabata, S. et al., "Evaluation of the Carboranyl porphyrin $H_2TCP$ as a Delivery Agent for Boron Neutron Capture Therapy (BNCT)," *Proceedings of the 13th World Congress of Neurological Surgery*, pp. 975-979 (2005).

Lauceri, R. et al., "Interactions of Anionic Carboranylated Porphyrins with DNA," *J. Am. Chem. Soc.*, vol. 123, pp. 5835-5836 (2001).

Luguya, R. et al., "Synthesis and Cellular Studies of a Carboranylchlorin for the PDT and BNCT of Tumors," *Bioorganic and Medicinal Chemistry*, vol. 14, pp. 5890-5897 (2006).

Luguya, R. et al., "Synthesis and Reactions of *meso*-(p-Nitrophenyl)porphyrins," *Tetrahedron*, vol. 60, pp. 2757-2763 (2004).

Luguya, R. et al., "Synthesis of Novel Carboranylchlorins with Dual Application in Boron Neutron Capture Therapy (BNCT) and Photodynamic Therapy (PDT)," *Journal of Applied Radiation and Isotopes*, vol. 61, pp. 1117-1123 (2004).

Luguya, R.J. et al., "Carboranylcorroles," *Tetrahedron Letters*, vol. 46, pp. 5365-5368 (2005).

Luo, Y. et al., "Initiation of Apoptosis versus Necrosis by Photodynamic Therapy with Chloroaluminum Phthalocyanine," *Photochem. Photobiol*, vol. 66, No. 4, pp. 479-483 (1997).

Maderna, A. et al., "Synthesis of a porphyrin-labelled carboranyl phosphate diester: a potential new drug for boron neutron capture therapy of cancer," Chem. Commun., pp. 1784-1785 (2002).

Ongayi, O. et al., "Synthesis and Characterization of a Carboranyl-tetrabenzoporphyrin," *Bioorganic and Medicinal Chemistry Letters*, vol. 15, pp. 1665-1668 (2005).

Pignol, J.-P. et al., "Selective Delivery of $^{10}B$ to Soft Tissue Sarcoma Using $^{10}B$-L-borophenylalanine for Boron Neutron Capture Therapy," *Br. J. Radiol.*, vol. 71, pp. 320-323 (1998).

Renner, M.W. et al., "Recent Progress in the Syntheses and Biological Evaluation of Boronated Porphyrins for Boron Neutron-Capture Therapy," NCT, *Anti-Cancer Agents in Med. Chem.*, vol. 6. pp. 145-158 (2006).

Schnitmaker, J. J. et al., "Photodynamic Therapy: a Promising New Modality for the Treatment of Cancer," *Photochem. Photobiol. B: Biol.*, vol. 34, pp. 3-12 (1996).

Sibrian-Vazquez, M. et al., "Enhanced Cellular Uptake with a Cobaltacarborane-Porphyrin-HIV-1 Tat 48-60 Conjugate," *Bioconjugate Chem.*, vol. 17, pp. 928-934 (2006).

Vicente, M.. et al., "First Structural Characterization of a Covalent Bonded Porphyrin-Carborane System," *Chemical Communications*, pp. 483-484 (2001).

Vicente, M., "Porphyrin-based sensitizers in the detection and treatment of cancer: recent progress," Curr. Med. Chem., vol. 1, pp. 175-194 (2001).

Vicente, M.. et al., "Singlet Oxygen Generation and Dark Toxicity of a *nido*- and a *closo*-Carboranylporphyrin," *Proceedings of SPIE, The International Society for Optical Engineering*, vol. 5315, pp. 33-40 (2004).

Vicente, M. et al., "Syntheses and preliminary biological studies of four *meso*-tetra[(nido-carboranylmethyl)phenyl]porphyrins," Bioorganic & Medicinal Chem., vol. 10, pp. 481-492 (2002).

Vicente, M. et al., "Syntheses of carbon-carbon linked carboranylated porphyrins for boron neutron capture therapy of cancer," *Tetr. Lett.*, vol. 41, pp. 7623-7627 (2000).

Vicente M. et al., "Syntheses of Phosphonate- and Amine-substituted Carboranylporphyrins for Boron Neutron Capture Therapy of Tumors," *Proceedings for the 12th International Symposium on Neutron Capture Therapy for Cancer*, pp. 231-233 (2006).

Vicente, M. et al., "Synthesis, Dark Toxicity and Induction of in vitro DNA Photodamage by a Tetra(4-nido-carboranylphenyl)porphyrin," *Journal of Photochemistry and Photobiology B: Biology*, vol. 68, pp. 123-132 (2002).

Vicente, M. et al., "Syntheses, Toxicity and Biodistribution of two 5,15-Di[3,5-(*nido*-carboranylmethyl)phenyl]porphyrin in EMT-6 Tumor Bearing Mice," *Bioorganic and Medicinal Chemistry*, vol. 11, pp. 3101-3108 (2003).

\* cited by examiner

BORON-CONTAINING PORPHYRIN COMPOUNDS AND THEIR USES

This is the United States national stage of international application PCT/US2006/041396, international filing date 25 Oct. 2006, which claims the benefit of the 25 Oct. 2005 filing date of provisional patent application 60/730,331 under 35 U.S.C. §119(e).

The development of this invention was partially funded by the United States Government under grant R01 CA098902 awarded by the National Institutes of Health, and grant CHE-304833 awarded by the National Science Foundation. The United States Government has certain rights in this invention.

TECHNICAL FIELD

This invention pertains to boron-containing porphyrin compounds, and their uses in fields including boron neutron capture therapy of tumors, radiotherapy of tumors, photodynamic therapy of tumors and other diseased tissue, imaging tissues, and inactivation of bacteria and viruses.

BACKGROUND ART

Boron neutron capture therapy (BNCT) is a bimodal radiation treatment for cancer treatment. $^{10}$B-rich tumors are irradiated with low-energy (e.g., thermal or epithermal) neutrons. A $^{10}$B nucleus absorbs a neutron and ejects an energetic (1.47 MeV) α particle ($^{4}$He$^{2+}$), a 0.84 MeV lithium ion ($^{7}$Li$^{3+}$), and a 0.48 MeV γ-ray. The $^{10}$B(n, α)$^{7}$Li nuclear reaction products are highly damaging to tumor cells through ionization processes, yet are of sufficiently low energy that they lie in the "Linear Energy Transfer" (LET) regime. See generally Barth, R. F., Soloway, A. H., Fairchild, R. G. & Brugger, R. M., Cancer, 1992, 70, 2995-3007; and Barth, R. F., Soloway, A. H., Goodman, J. H., Gahbauer, Fairchild, R. A, Gupta, N., Blue, T. E., Yang, W. & Tjarks, W., Neurosurg. 1999, 44, 433-451; and R. Barth et al., "Boron Neutron Capture Therapy of Cancer: Current Status and Future Prospects," Clin. Canc. Res., vol. 11, pp. 3987-4002 (2005); and published international patent application WO 01/85736. The nuclear reaction's energy E is nearly linear with distance x from the irradiated $^{10}$B nucleus, and dE/dx is large and negative. Cytotoxic ions resulting from the $^{10}$B(n, α)$^{7}$Li nuclear reaction travel only approximately 5 to 9 μm, about one cell diameter, effectively limiting toxicity to the cell in which the $^{10}$B nucleus was irradiated, and perhaps its nearest neighbors. BNCT has the potential for selectively targeting and destroying malignant cells in the presence of normal cells, provided a tumor-selective $^{10}$B-delivery drug is available. Such localized cancer therapies are particularly attractive for (but are not limited to) the treatment of high-grade gliomas and metastatic brain tumors, which infiltrate the brain, and for which selective tumor destruction could dramatically increase patient life quality and expectancy.

While $^{10}$B is not the only nuclide with a large neutron capture cross section, it is considered promising for neutron capture therapy due to the LET localization of the $^{10}$B(n, α)$^{7}$Li reaction's cytotoxic products, the nearly 20% abundance of $^{10}$B in naturally-occurring boron, boron's own non-radioactivity, and finally its chemical facility. It is possible to obtain boron compounds that are enriched in $^{10}$B up to 98%.

Exploitation of the $^{10}$B(n, α)$^{7}$Li reaction products' localized damage relies upon the preferential uptake of boron by tumor cells over that by healthy cells so that a concomitantly higher dose will be delivered during neutron irradiation. See Hawthorne, M. F., Mol. Med. Today, 1998, 4, 174-181; and Hawthorne, M. F., Angew. Chem. Int. Ed. Engl., 1993, 32, 950-984.

Two compounds, disodium mercapto-closo-dodecaborate (BSH) and L-4-dihydroxy-borylphenylalanine (BPA), have recently been employed in clinical trials in the United States, Europe, and Japan in patients with glioblastomas and melanomas. See Kageji, T., Nakagawa, Y, Kitamura, K., Matsumoto, K. & Hatanaka, H. J., Neurooncol. 1997, 33, 117-130; Pignol, J.-P., Oudart, H., Chauvel, P., Sauerwein, W, Gabel, D. & Prevot, G. Br. J. Radiol., 1998, 71, 320-323; and Elowitz, E. H., Bergland, R. M., Coderre, J. A, Joel, D. D., Chadha, M. & Chanana, A. D., Neurosurgery, 1998, 42, 45 463-469. BSH and BPA yield tumor: blood boron concentration ratios of about 1:1 and about 3:1, respectively. There is an unfilled need for new $^{10}$B carriers with improved tumor selectivity.

Porphyrins and related macrocycles tend to accumulate preferentially in neoplastic tissue over healthy tissue. See Bonnett, R. Chem. Soc. Rev., 1995, 24, 19-33.

Porphyrins are also useful in another therapeutic method, photodynamic therapy (PDT) of tumors. See Schnitmaker, J. J., Bass, P., van Leengoed, M. L. L. M., van der Meulen, F. W., Star, W. M. & van Zaudwijk, N.J., Photochem. Photobiol B: Biol., 1996, 34, 3-12; and Dougherty, T. J., Gomer, C. J., Henderson, B. W., Jori, G., Kessel, D., Korbelik, M., Moan, J. & Peng, Q. J., Natl. Cancer Inst., 1998, 90, 889-905. PDT relies upon the selective uptake into tumor tissues of the compound, which will now act as a photosensitizer. After tissue uptake, irradiation with light causes the generation of highly-reactive singlet oxygen ($^{1}$O$_{2}$) and other cytotoxins. For example, Photofrin® is an FDA-approved, porphyrin derivative that has been used in photodynamic therapy for cancers of the lung, digestive tract, and genitourinary tract.

Another porphyrin-based drug, Visudyne™, has been approved by the FDA to suppress the development of choroidal neovascular membranes, the leaky vascular structures that cause age-related ("wet") macular degeneration of the eye. The $^{1}$O$_{2}$ coagulates blood within the neovascular network, thereby clogging and killing it.

Some porphyrins also appear to suppress cancer by a mechanism less harsh than oxidatively-driven necrosis, and instead to induce apoptosis, the orderly shutdown, death, and absorption of cells mediated by the immune system. This mechanism appears to work either upon irradiation with light, particularly at low levels, or by mere accumulation of high drug levels in tissues, even without light irradiation. See Luo Y, Chang, C. K. & Kessel, D., Photochem. Photobiol. 1996, 63, 4, 528-534; Luo Y & Kessel, D., Photochem. Photobiol. 1997, 66, 4, 479-483. The ability of porphyrin-derived drugs to induce apoptosis may enhance the effectiveness of both PDT and BNCT cancer treatments.

A potential advantage of epithermal neutron-based BNCT over PDT is that, while the red light required for PDT penetrates only several millimeters in tissue, epithermal neutrons penetrate effectively to depths of 5-7 cm. Another distinguishing aspect of BNCT is that the energetic $^{7}$Li and α particles formed by the neutron capture reaction do not require oxygen to maximize their toxicity, and can mitotically disable quiescent malignant cells in poorly oxygenated parts of a tumor. However, PDT has the advantage of using readily-available and relatively safe laser radiation. Furthermore, significantly lower doses of porphyrin are required for PDT than for BNCT.

M. Vicente, "Porphyrin-based sensitizers in the detection and treatment of cancer: recent progress," Curr. Med. Chem., vol. 1, pp. 175-194 (2001) provides a review of the use of porphyrins for cancer detection and treatment by photodynamic therapy, boron neutron capture therapy, radiation therapy, and magnetic resonance imaging.

M. Vicente et al., international patent application WO 01/85736 (2001), discloses the use of certain porphyrin-based compounds for BNCT. See also M. Vicente et al., "Syntheses and preliminary biological studies of four meso-tetra[(nido-carboranylmethyl)phenyl]porphyrins," Bioorganic & Medicinal Chem., vol. 10, pp. 481-492 (2002); A. Maderna et al., "Synthesis of a porphyrin-labeled carboranyl phosphate diester: a potential new drug for boron neutron capture therapy of cancer," Chem. Commun., pp. 1784-1785

(2002); M. Vicente et al., "Syntheses of carbon-carbon linked carboranylated porphyrins for boron neutron capture therapy of cancer," Tetr. Lett., vol. 41, pp. 7623-7627 (2000); and M. Vicente et al., "Synthesis, dark toxicity and induction of in vitro DNA photodamage by a tetra(4-nido-carboranyl)porphyrin," J. Photochemistry and Photobiology. Vol. 68, pp. 123-132 (2002).

DISCLOSURE OF INVENTION

We have discovered novel boron-containing porphyrin compounds. The novel compounds may be used in fields such as boron neutron capture therapy of tumors, radiotherapy of tumors, photodynamic therapy of tumors, imaging tissues, and inactivating bacteria and viruses.

In one aspect of this invention, novel metallocarborane-substituted porphyrins and derivatives are synthesized in high yields. The metal atom in these compounds may be cobalt or another metal (e.g., Al, Au, Co, Cr, Cu, Fe, Ni, Mn, Pt), or a radioisotope of such a metal atom (e.g., $^{57}$Co). The metallocarborane moieties are attached to the porphyrin ring via the meso carbons (one or more of carbon atoms 5, 10, 15, and 20), or via an inner nitrogen atom. The novel compounds have a higher selectivity for tumor tissue than that of most previous metallocarboranes. Conjugating a metallocarborane to a porphyrin macrocycle provides high selectivity for tumors, and low toxicity to normal tissue.

In another aspect of this invention, novel boron-containing tetrabenzoporphyrins are synthesized in high yields. These compounds may be used in PDT or BNCT of tumors. Preliminary experimental results have shown that these compounds and their derivatives have low toxicity and high selectivity for tumor cells, and are efficient sensitizers for both PDT and BNCT. These compounds may be used, for example, in treating malignant brain tumors. Previously-reported boron-containing porphyrins have absorbed red light only weakly, which is a disadvantage because longer wavelengths of light penetrate tissue more deeply than do short wavelengths. Tetrabenzoporphyrins (TBPs) have extended conjugated π systems, and strongly absorb red wavelengths. They are taken up by tumor cells, including brain tumor cells, with high avidity. These compounds have low toxicity to normal cells. The novel compounds should be less susceptible to enzymatic hydrolysis than prior compounds with ester linkages.

In another embodiment, the compounds of this invention may be used in tissue imaging, e.g., autoradiography, MRI and conventional x-ray radiography. In another embodiment, the compounds may be used to inactivate bacteria, viruses, and other pathogens by activation with visible light.

The novel compounds may be used not only in boron neutron capture therapy, but also in photodynamic therapy of tumors. When the compounds are administered in vivo, subsequent exposure of targeted tissue to actinic light (especially red light) produces reactive singlet oxygen in situ, leading to cell death via necrosis or apoptosis.

MODES FOR CARRYING OUT THE INVENTION

Figure 1:
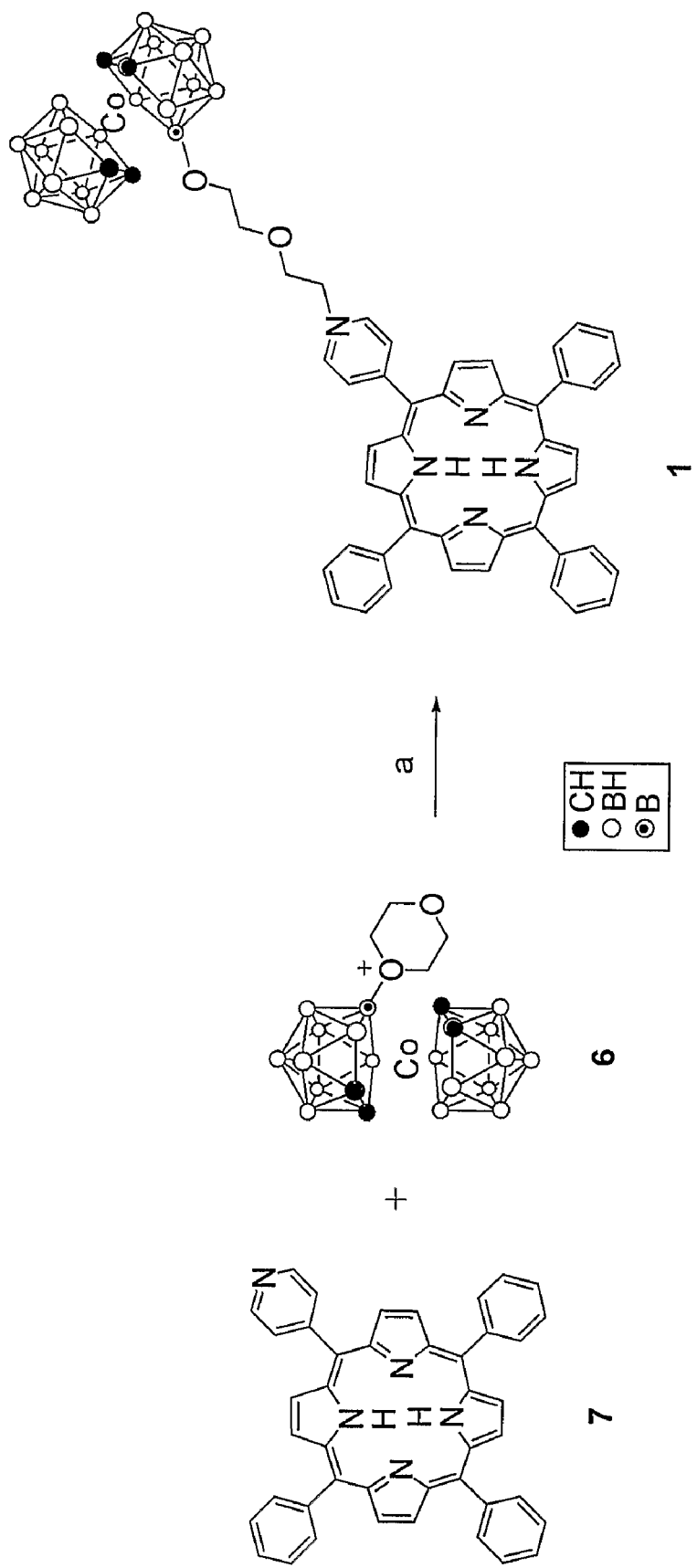
FIG. 1 depicts a reaction scheme leading to Compound 1.
Figure 2:
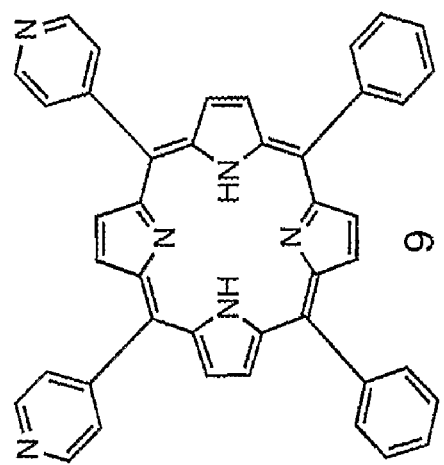
FIG. 2 depicts pyridyl porphyrin derivatives used as starting materials for Compounds 2-5.
Figure 2:
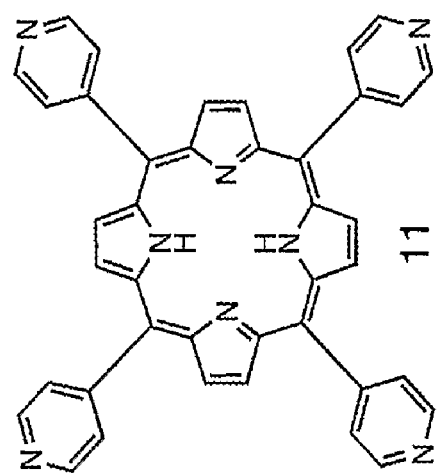
Figure 2:
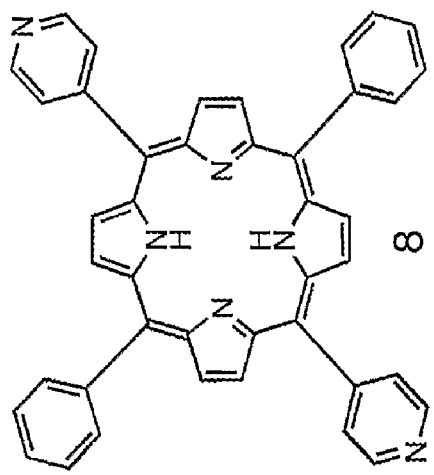
Figure 2:
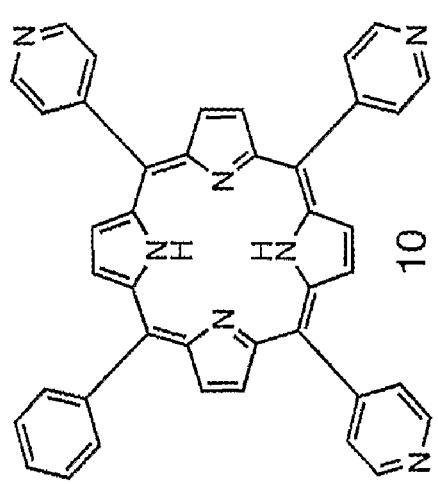
Figure 3:
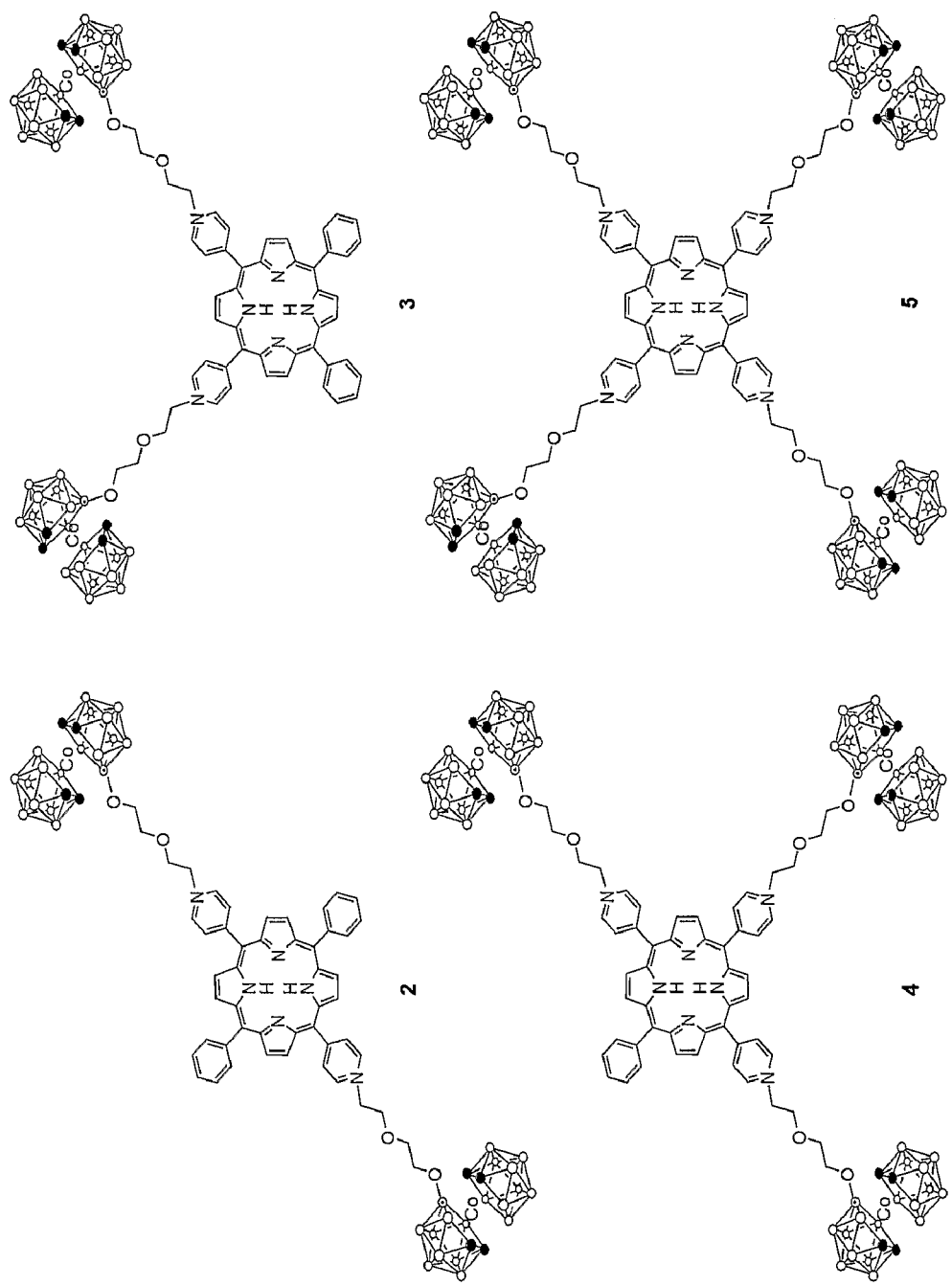
FIG. 3 depicts Compounds 2-5.
Figure 4:
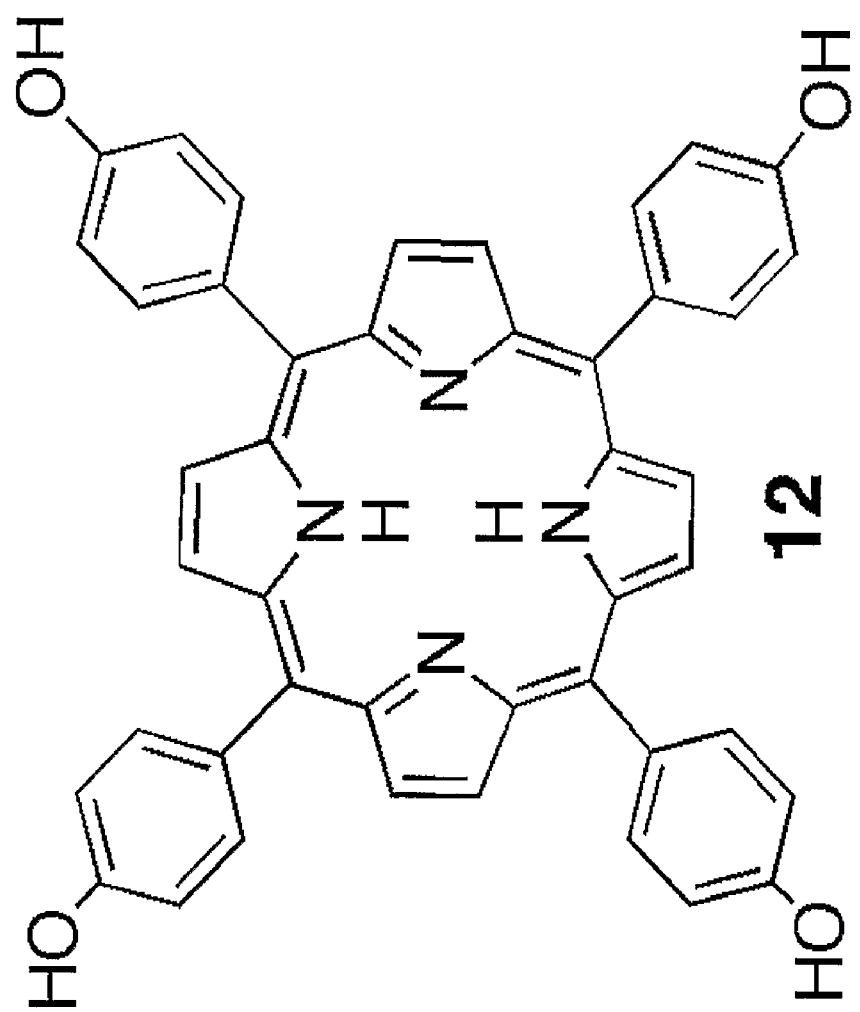
FIG. 4 depicts phenolic porphyrin derivative 12, which was used as the starting material for Compound 13.
Figure 5:
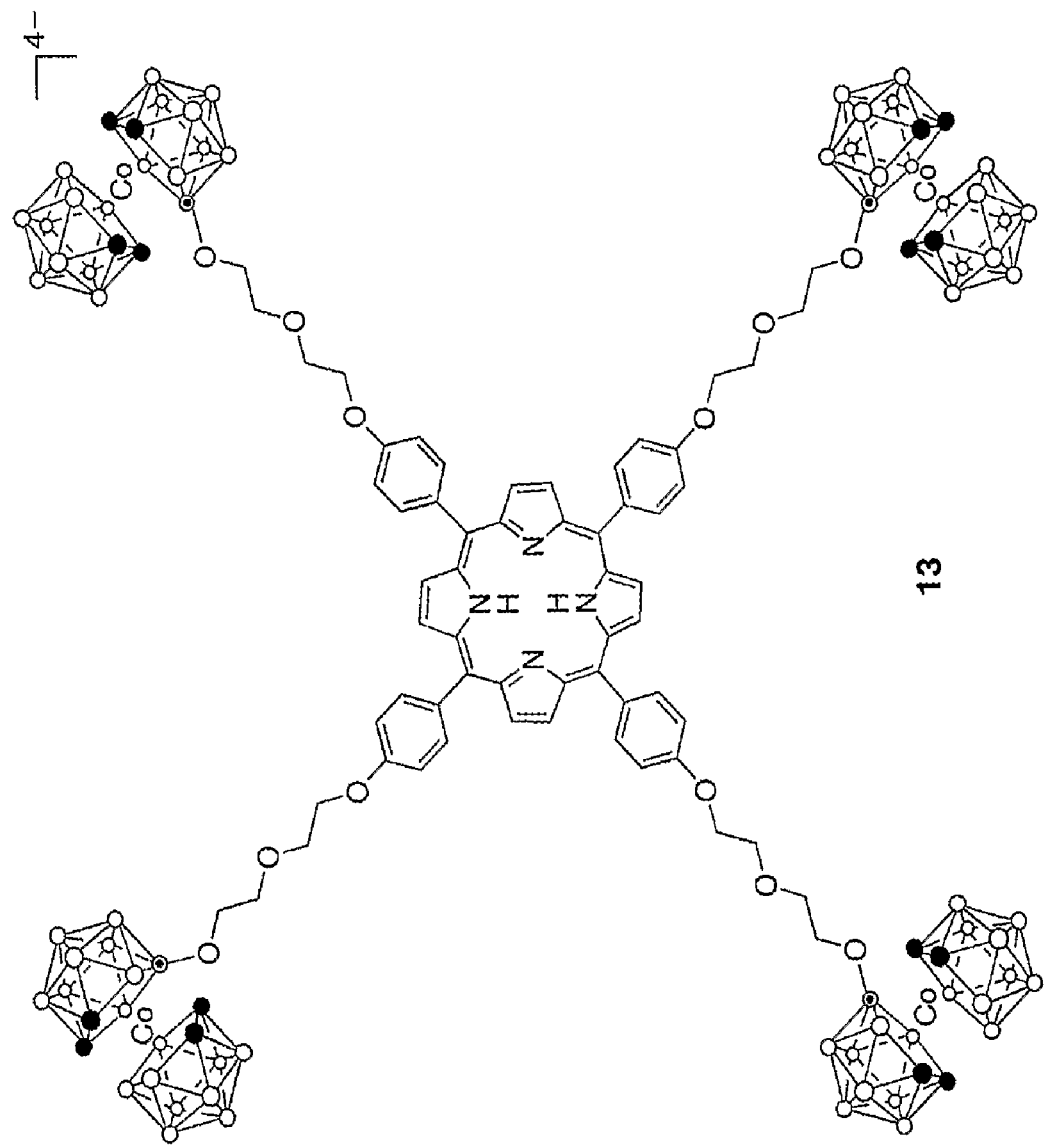
FIG. 5 depicts Compound 13.
Figure 6:
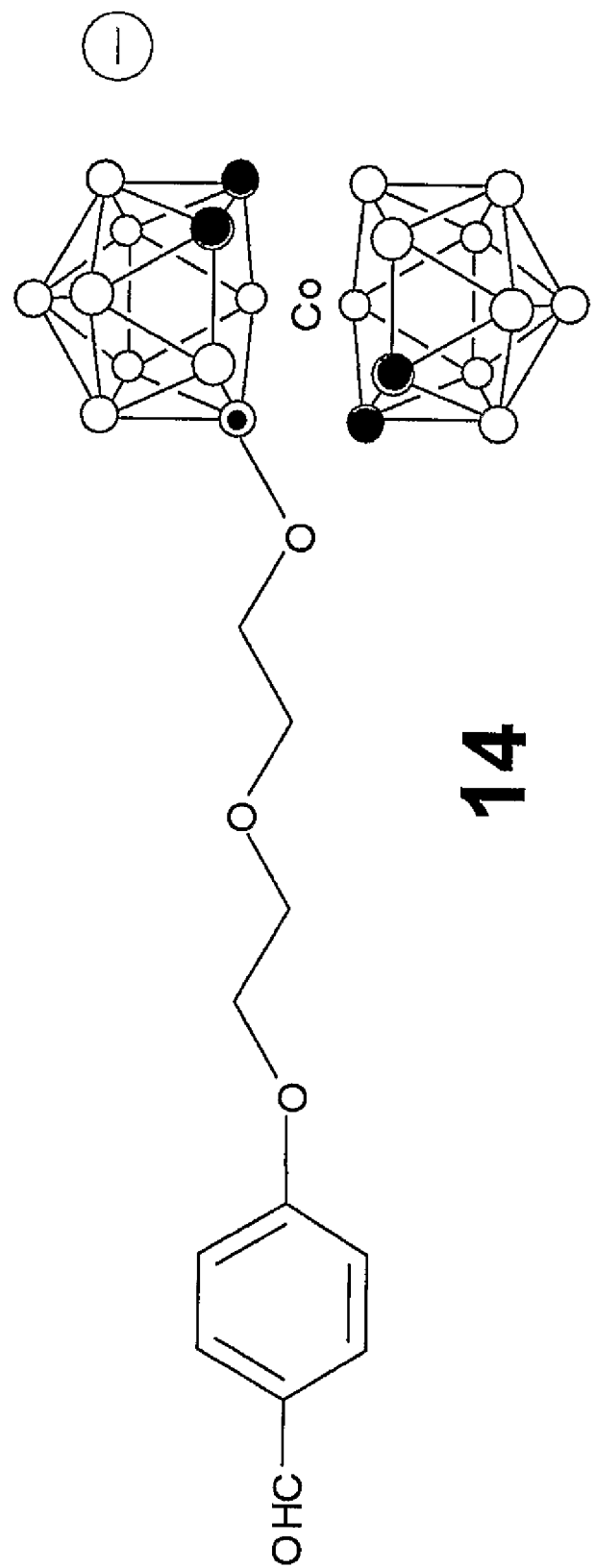
FIG. 6 depicts an aldehyde used as a starting material in an alternative synthesis of Compound 13.
Figure 7:
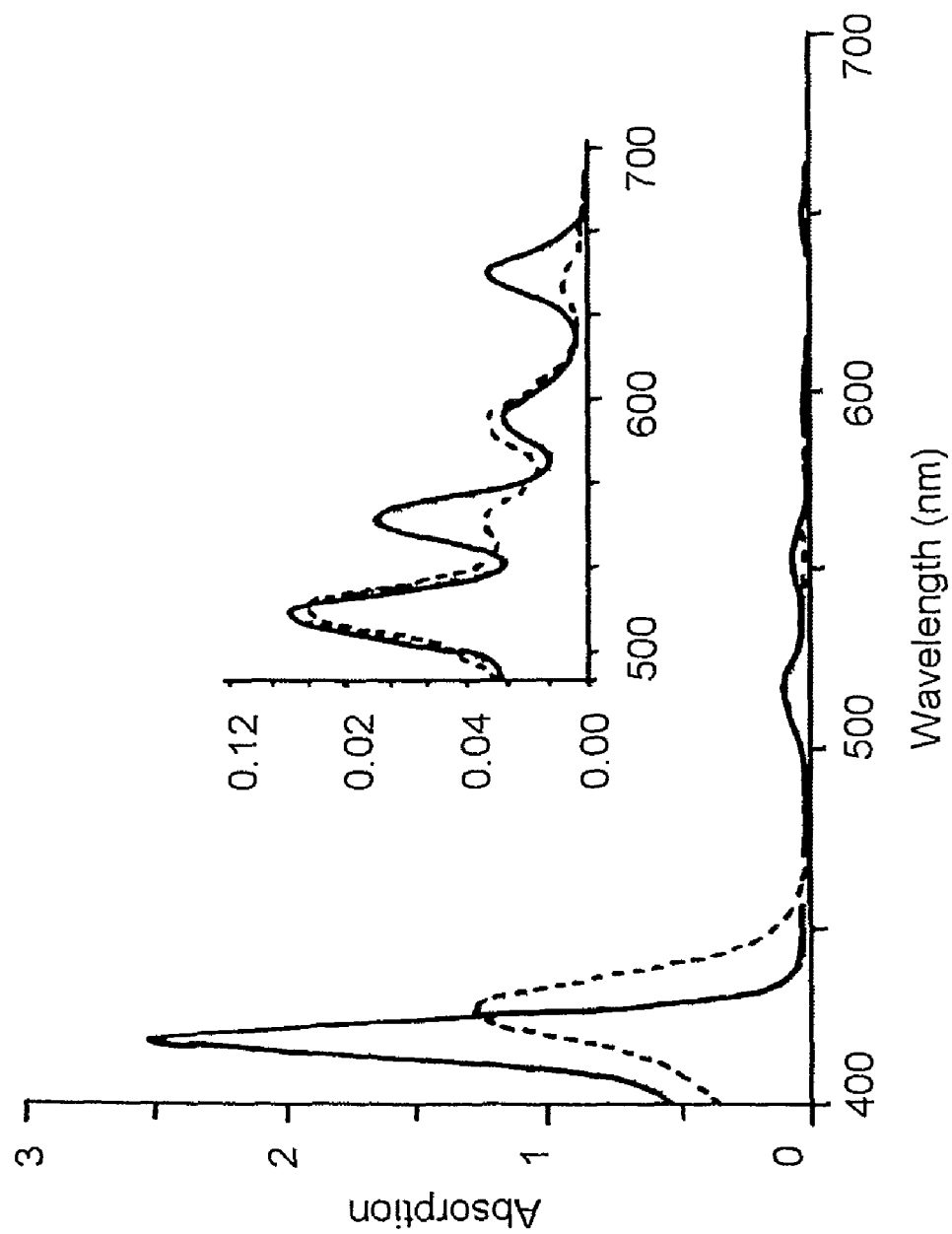
FIG. 7 depicts optical spectra of porphyrins 13 (full line) and 5 (dashed line) at a concentration of 6×10$^{-6}$ M in acetone solution.

The total syntheses of five new porphyrin-cobaltacarborane conjugates (Compounds 1-5) have been achieved in 88-98% yields in a single step reaction between a nucleophilic meso-pyridyl-containing porphyrin and a zwitterionic cobaltacarborane [3,3'-Co(8-$C_4H_8O_2$-1,2-$C_2B_9H_{10}$)(1',2'-$C_2B_9H_{11}$)]. These unique zwitterionic compounds have one to four cobaltabisdicarbollide anions conjugated to a porphyrin macrocycle via $(CH_2CH_2O)_2$ chains. Cellular uptake, cytotoxicity, and intracellular localization of the cobaltacarboraneporphyrins 1-5 were observed in human HEp2 cells. The initial observations suggest that Compounds 1-5 will be useful as chemotherapy agents. The number and distribution of cobaltacarborane residues linked to the porphyrin macrocycle had a significant effect on the cellular uptake of the conjugates.

Water-soluble nido-carboranyl-tetrabenzoporphyrins have also been synthesized in 43% overall yield, by condensation of butanopyrrole with a carboranylbenzaldehyde, followed by metal insertion, oxidation, demetallation and deboronation. These compounds were found to accumulate within human glioblastoma T98G cells to a significant higher extent than a structurally related nido-carboranylporphyrin, and to localize preferentially in intracellular lysosomes. Animal toxicity studies using male and female BALB/c mice found both compounds to be non-toxic even at a dose of 160 mg/kg, administered intraperitoneally as a single injection at a concentration of 4 mg/mL. Tetra(carboranylphenyl)-tetrabenzoporphyrin and related compounds are promising new sensitizers for the treatment of malignant tumors.

In comparison with carboranylporphyrin 20, TBP 19 showed a significantly higher uptake in human glioblastoma T98G cells in vitro, probably as a result of its higher hydrophobic character due to its four β,β'-porphyrin fused benzene rings. The cellular uptake of TBP 19 and porphyrin 20 were concentration- and time-dependent, systematically increasing with both the concentration and time of exposure to T98G cells. The preferential sites of intracellular localization of TBP 19 are the lysosomes, as has been previously observed for negatively charged carboranylporphyrins. Both TBP 19 and porphyrin 20 were non-toxic to BALB/c mice, even at the high dose of 160 mg/kg administered in a single i.p. injection. No clinical, biochemical, or histopathological effects were observed which could be attributed to the administration of TBP 19, porphyrin 20 or the vehicle used. Our results suggest that TBP 19 is a promising new sensitizer for the treatment of malignant tumors by BNCT and/or PDT.

In another embodiment of the invention, cobaltacarborane linkages are made directly to the porphyrin ring's inner nitrogen atoms. One advantage of such a structure is steric interference with the aromatic rings' π-π stacking, which can help reduce microaggregate formations. The formation of microaggregates has been a problem with other groups of compounds.

Additional compounds that are within the scope of the present invention include those having the following structure:

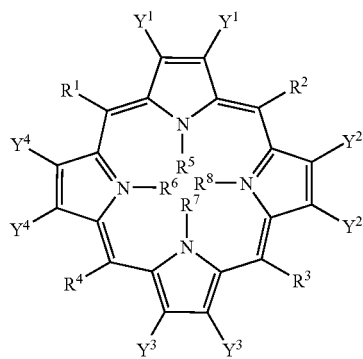

In the above structure, the $R^1$-$R^4$ groups may be the same or different, and may be selected from the group consisting of hydrogen, substituted or unsubstituted phenyl, pyridyl, hydroxyphenyl, 4-($C_2B_9H_{11}$)phenyl, or other aromatic groups, metallobisdicarbollides, or carboranylphenyl groups. Examples include: $C_6H_5$; $C_6H_5O$; $C_7H_7O$; $C_5H_4N$; $C_6H_4O(CH_2CH_2O)_2[Co(C_2B_9H_{11})_2]$; $C_5H_4N(CH_2CH_2O)_2[Co(C_2B_9H_{11})_2]$; $C_6H_3\{O(CH_2CH_2O)_2[Co(C_2B_9H_{11})_2]\}_2$; 4-(carboranyl)phenyl; 3-(carboranyl)phenyl; (carboranylmethyl)phenyl; 3-(carboranylmethyl)phenyl; and 3,5-di(carboranylmethyl)phenyl. The Groups $R^5$, $R^6$, $R^7$ or $R^8$ may be the same or different, and may be hydrogen, metal, or $(CH_2CH_2O)_2[Co(C_2B_9H_{11})_2]$. Examples of suitable metal atoms include Zn(II), Cu(II), Ni(II), Pd(II), Al(III), Sn(IV), Ga(III), Si(IV), Ge(IV), In(III), or Gd(III).

The two $Y^1$ groups are the same, as are the two $Y^2$s, the two $Y^3$s and the two $Y^4$s. The several groups $Y^1$, $Y^2$, $Y^3$ and $Y^4$ may be the same or different from one another. They may individually be, for example, hydrogen, or —CH═CH—CH═CH— or a small alkyl group, such as methyl, ethyl, propyl, isopropyl, or butyl. If, in particular, the two $Y^n$ groups together are —CH═CH—CH═CH—, then that means the compound contains a fused benzene ring at those positions.

EXAMPLE 1

Starting Materials, and Analyses. All syntheses were monitored by TLC using 0.25 mm silica gel plates, with or without UV indicator (Merck 60F-254). Silica gel from Sorbent Technologies, 32-63 μm, was used for flash column chromatography. $^1$H— and $^{13}$C-NMR were obtained on either a DPX-250 or a ARX-300 Bruker spectrometer. Chemical shifts (δ) are given in ppm relative to acetone-$d_6$ (2.05 ppm, $^1$H; 207.07 ppm, $^{13}$C), unless otherwise indicated. Electronic absorption spectra were measured on a Perkin Elmer Lambda 35 UV-Vis spectrophotometer. Fluorescence spectra were measured on a Perkin Elmer LS55 spectrometer. Mass spectra were obtained on an Applied Biosystems QSTAR XL. All solvents were purchased from Fisher Scientific (HPLC grade) and used without further purification. Zwitterionic [3,3'-Co(8-$C_4H_8O_2$-1,2-$C_2B_9H_{11}$)(1',2'-$C_2B_9H_{11}$)] (Compound 6) was prepared from the cesium salt of cobaltabisdicarbollide, obtained from Katchem Ltd (Czech Republic). The 5-(4'-pyridyl)-10,15,20-triphenylporphyrin (Compound 7), trans-5,15-di(4'-pyridyl)-10,20-diphenylporphyrin (Compound 8), cis-5,10-di(4'-pyridyl)-15,20-diphenylporphyrin (Compound 9), and 5,10,15-tri(4'-pyridyl)-20-phenylporphyrin (Compound 10) were prepared as known in the art. 5,10,15,20-Tetra(4'-pyridyl)porphyrin (Compound 11) was obtained from Sigma-Aldrich and recrystallized from chloroform/methanol before use.

EXAMPLE 2

Synthesis of Compound 1: 5-(4'-Cobaltacarboranepyridyl)-10,15,20-triphenylporphyrin Porphyrin 7 (61.6 mg, 0.10 mmol) and compound 6 (61.5 mg, 0.15 mmol) were heated in 40 mL of chloroform/acetonitrile 1:1 for 12 h. Compound 1 was obtained in 98.4% yield (101.0 mg) as a purple solid. UV-Vis (acetone) $\lambda_{max}$ ($\epsilon$/M$^{-1}$cm$^{-1}$) 418 (157,600), 515 (10,100), 551 (5,300), 590 (3,400), 646 (2,600). $^1$H NMR (acetone-$d_6$): δ 9.73 (d, 2H, J=6.7 Hz, o-PyrH), 9.10-9.07 (m, 4H, b-H), 9.00 (d, 2H, J=4.8 Hz, m-PyrH), 8.90 (s, 4H, b-H), 8.28-8.24 (m, 6H, o-PhH), 7.86-7.76 (m, 9H, m,p-PhH), 5.34-5.30 (m, 2H, NCH$_2$), 4.51-4.42 (m, 2H, OCH$_2$), 4.06-4.03 (m, 4H, OCH$_2$), 3.84-3.82 (br s, 4H, carborane-H), 1.6-3.0 (br, 17H, BH), −2.74 (s, 2H, NH). $^{13}$C NMR (acetone-$d_6$): δ 160.1, 144.8, 142.2, 135.1, 133.6, 128.9, 127.7, 1230, 122.1, 113.3, 73.0, 69.7, 61.8, 52.5, 46.9. HRMS (MALDI-TOF) m/z 1026.5713, calculated for $C_{51}B_{18}H_{58}N_5O_2Co$ 1026.5739.

EXAMPLE 3

Synthesis of Compound 2: trans-5,15-di(4'-cobaltacarboranepyridyl)-10,20-diphenylporphyrin Porphyrin 8 (16.0 mg, 0.026 mmol) and compound 6 (43 mg, 0.10 mmol) were heated in 40 mL of chloroform/acetonitrile 1:1 for two days, yielding 34.1 mg (91.1%) of Compound 2. UV-Vis (acetone) $\lambda_{max}$ ($\epsilon$/M$^{-1}$cm$^{-1}$) 422 (129,400), 516 (8,400), 554 (5,200), 590 (3,400), 651 (2,800). $^1$H NMR (acetone-$d_6$): δ 9.76 (d, 4H, J=6.7 Hz, o-PyrH), 9.13-9.09 (m, 8H, b-H), 9.04 (d, 4H, J=4.9 Hz, m-PyrH), 8.29-8.26 (m, 4H, o-PhH), 7.91-7.83 (m, 6H, m,p-PhH), 5.34-5.32 (br m, 4H, NCH$_2$), 4.44-4.42 (br m, 4H, OCH$_2$), 4.06 (br s, 4H, OCH$_2$), 4.02 (br s, 4H, OCH$_2$), 3.87-3.83 (m, 8H, carborane-H), 1.6-3.0 (br, 34H, BH), −2.80 (s, 2H, NH). $^{13}$C NMR (acetone-$d_6$): δ 160.0, 145.3, 142.2, 135.5, 133.8, 129.5, 128.2, 123.2, 115.5, 73.7, 70.4, 62.6, 53.1, 47.6. HRMS (MALDI-TOF) m/z 1438.9027, calculated for $C_{58}B_{36}H_{86}N_6O_4Co_2$ 1438.8987.

EXAMPLE 4

Synthesis of Compound 3: cis-5,10-di(4'-cobaltacarboranepyridyl)-15,20-diphenylporphyrin Porphyrin 9 (16.0 mg, 0.026 mmol) and compound 6 (43 mg, 0.10 mmol) were heated in 40 mL of chloroform/acetonitrile 1:1 for two days, affording 33.5 mg (91.0%) of Compound 3. UV-Vis (acetone) $\lambda_{max}$ ($\epsilon$/M$^{-1}$cm$^{-1}$) 423 (141,000), 518 (10,600), 553 (5,000), 590 (4,000), 645 (1,600). $^1$H NMR (acetone-$d_6$): δ 9.75 (d, 4H, J=6.7 Hz, o-PyrH), 9.18 (s, 2H, m-PyrH), 9.11 (d, 6H, J=6.7 Hz, b-H), 9.04 (d, 2H, J=4.9 Hz, b-H), 8.92 (s, 2H, m-PyrH), 8.27-8.23 (m, 4H, o-PhH), 7.85-7.82 (m, 6H, m,p-PhH), 5.33-5.31 (br m, 4H, NCH$_2$), 4.50-4.48 (br m, 4H, OCH$_2$), 4.09-4.03 (m, 8H, OCH$_2$), 3.86-3.81 (m, 8H, carborane-H), 1.6-3.0 (br, 34H, BH), −2.75 (s, 2H, NH). $^{13}$C NMR (acetone-$d_6$): δ 159.9, 145.3, 142.1, 135.4, 133.8, 129.4, 128.0, 124.2, 114.6, 73.6, 70.3, 70.2, 62.5, 53.0, 47.5. HRMS (MALDI-TOF) m/z 1438.8960, calculated for $C_{58}B_{36}H_{86}N_6O_4CO_2$ 1438.8987.

EXAMPLE 5

Synthesis of Compound 4: 5,10,15-Tri(4-cobaltacarboranepyridyl)-20-phenylporphyrin Porphyrin 10 (31.0 mg, 0.05 mmol) and compound 6 (100.3 mg, 0.24 mmol) were heated in 40 mL of chloroform/acetonitrile 1:1 for two days to yield 83.0 mg (90.0%) of Compound 4. UV-Vis (acetone) $\lambda_{max}$ ($\epsilon/M^{-1}cm^{-1}$) 425 (168,000), 516 (12,600), 553 (5,600), 591 (4,300), 647 (1,900). $^1$H NMR (acetone-$d_6$): δ 9.79-9.75 (m, 6H, o-PyrH), 9.21-9.19 (m, 6H, m-PyrH), 9.14-9.11 (m, 6H, b-H), 9.07 (d, 2H, J=5.8 Hzb-H), 8.29-8.25 (m, 2H, o-PhH), 7.91-7.86 (m, 3H, m,p-PhH), 5.34 (br s, 6H, NCH$_2$), 4.43 (br s, 6H, OCH$_2$), 4.04 (s, 6H, OCH$_2$), 3.99 (s, 6H, OCH$_2$), 3.84 (s, 12H, carborane-H), 1.6-3.0 (br, 51H, BH), −2.83 (s, 2H, NH). $^{13}$C NMR (acetone-$d_6$): δ 159.2, 145.2, 142.1, 135.2, 133.5, 129.4, 127.9, 124.2, 116.1, 73.4, 70.0, 62.3, 52.7, 47.3. HRMS (MALDI-TOF) m/z 1850.2320, calculated for $C_{65}B_{54}H_{114}N_7O_6CO_3$ 1850.2263.

EXAMPLE 6

Synthesis of Compound 5: 5,10,15,20-Tetra(4'-cobaltacarboranepyridyl)porphyrin Porphyrin 11 (17.0 mg, 0.027 mmol) and compound 6 (62.0 mg, 0.15 mmol) were heated in 40 mL of chloroform/acetonitrile 1:1 for three days, yielding 53.3 mg (87.7%) of Compound 5. UV-Vis (acetone) $\lambda_{max}$ ($\epsilon/M^{-1}cm^{-1}$) 427 (210,000), 517 (15,600), 553 (5,880), 590 (5,630), 645 (1,500). $^1$H NMR (acetone-$d_6$): d 9.80 (d, 8H, J=6.3 Hz, o-PyrH), 9.26 (s, 8H, b-H), 9.15 (d, 8H, J=6.3 Hz, m-PyrH), 5.36 (br s, 8H, NCH$_2$), 4.43 (br s, 8H, OCH$_2$), 4.05 (br s, 8H, OCH$_2$), 4.00 (br s, 8H, OCH$_2$), 3.86-3.84 (m, 16H, carborane-H), 1.6-3.0 (br, 68H, BH), −2.89 (s, 2H, NH). $^{13}$C-NMR (acetone-$d_6$): δ 159.4, 145.9, 134.1, 117.4, 74.0, 70.6, 70.5, 62.9, 53.3, 47.9. HRMS (MALDI-TOF) m/z 2262.5566, calculated for $C_{72}H_{142}N_8O_8B_{72}CO_4$ 2262.5509.

EXAMPLES 7-12

Syntheses of Compound 13: 5,10,15,20-Tetra(4'-cobaltacarborane 4-hydroxyphenyl)porphyrin, and salts; and Alternative Synthesis of Compound 5

The conjugation of 5,10,15,20-tetra(4-hydroxyphenyl) porphyrin 12 with cobaltacarborane 2 was achieved in 85% yield upon activation of the porphyrin hydroxyl groups with either cesium carbonate or potassium carbonate in anhydrous acetone, producing Compound 13 as the cesium or potassium salt. Similarly, the zwitterionic porphyrin conjugate Compound 5 was prepared in 88% yield upon refluxing 5,10,15, 20-tetra(4-pyridyl)porphyrin 4 in a 1:1 mixture of chloroform and acetonitrile, in the presence of an excess of Compound 2. Both reactions were monitored by TLC and $^1$H-NMR spectroscopy, and the target conjugates 13 (as the Cs or K salt) and 5 were purified by column chromatography on silica gel, using ethyl acetate/acetone mixtures for elution, followed by filtration on a Sephadex LH-20 column using methanol (for 13) or acetonitrile (for 5) as eluant. Alternatively, conjugate 13 was prepared, in 20% yield, from condensation of the aldehyde 14 with pyrrole, under Lindsey-type conditions (using BF$_3$.Et$_2$O as the catalyst and DDQ as the oxidizing agent). Aldehyde 14 was prepared in 90% yield from reaction of commercially-obtained 4-hydroxybenzaldehyde with cobaltacarborane 2 in the presence of potassium carbonate.

Figure 8:
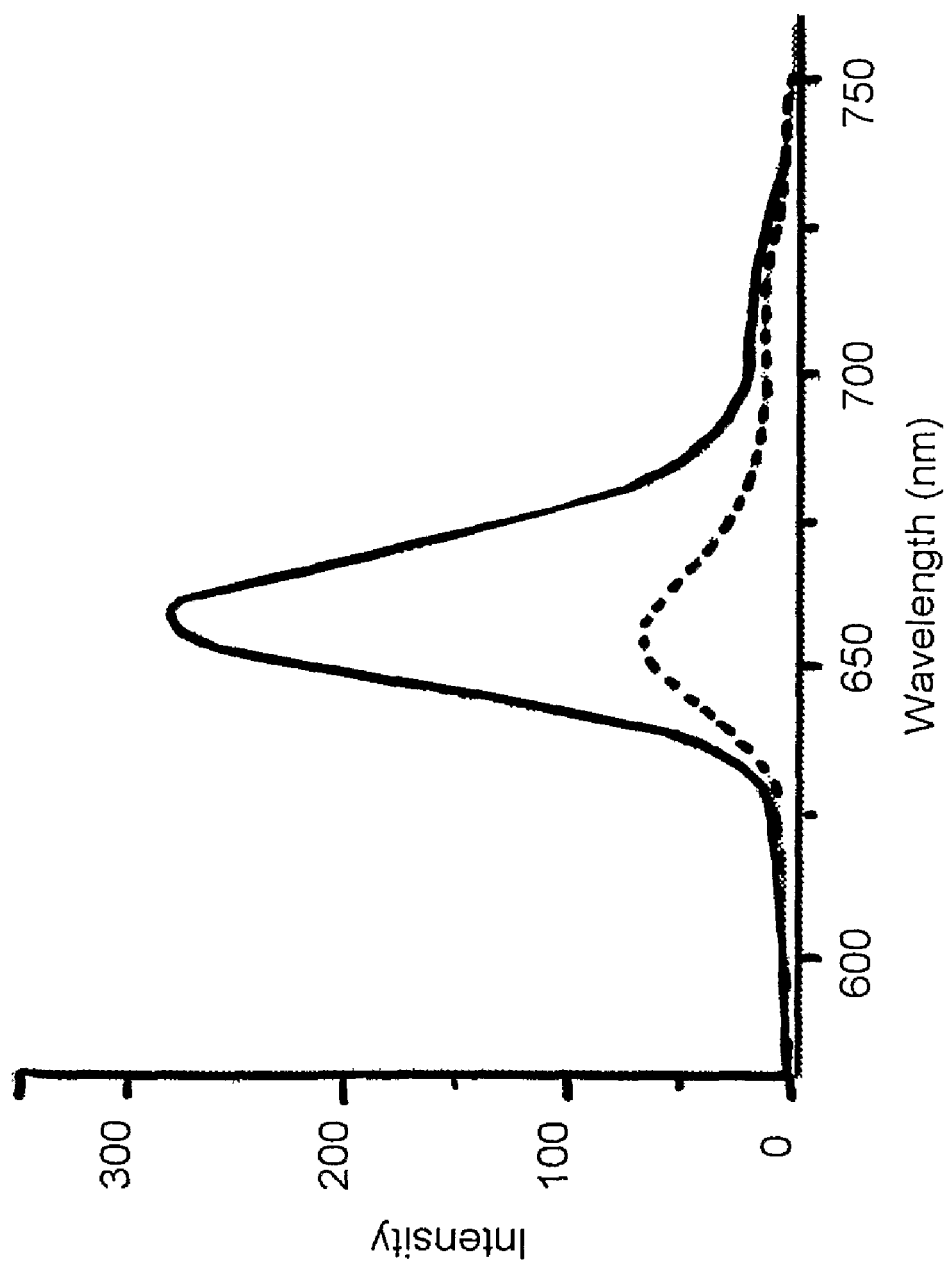
FIG. 8 depicts fluorescence emission spectra of porphyrins 13 (full line) and 5 (dashed line) at a concentration of 6×10$^{-6}$ M in acetone solution (excitation at 512 nm).
Figure 9:
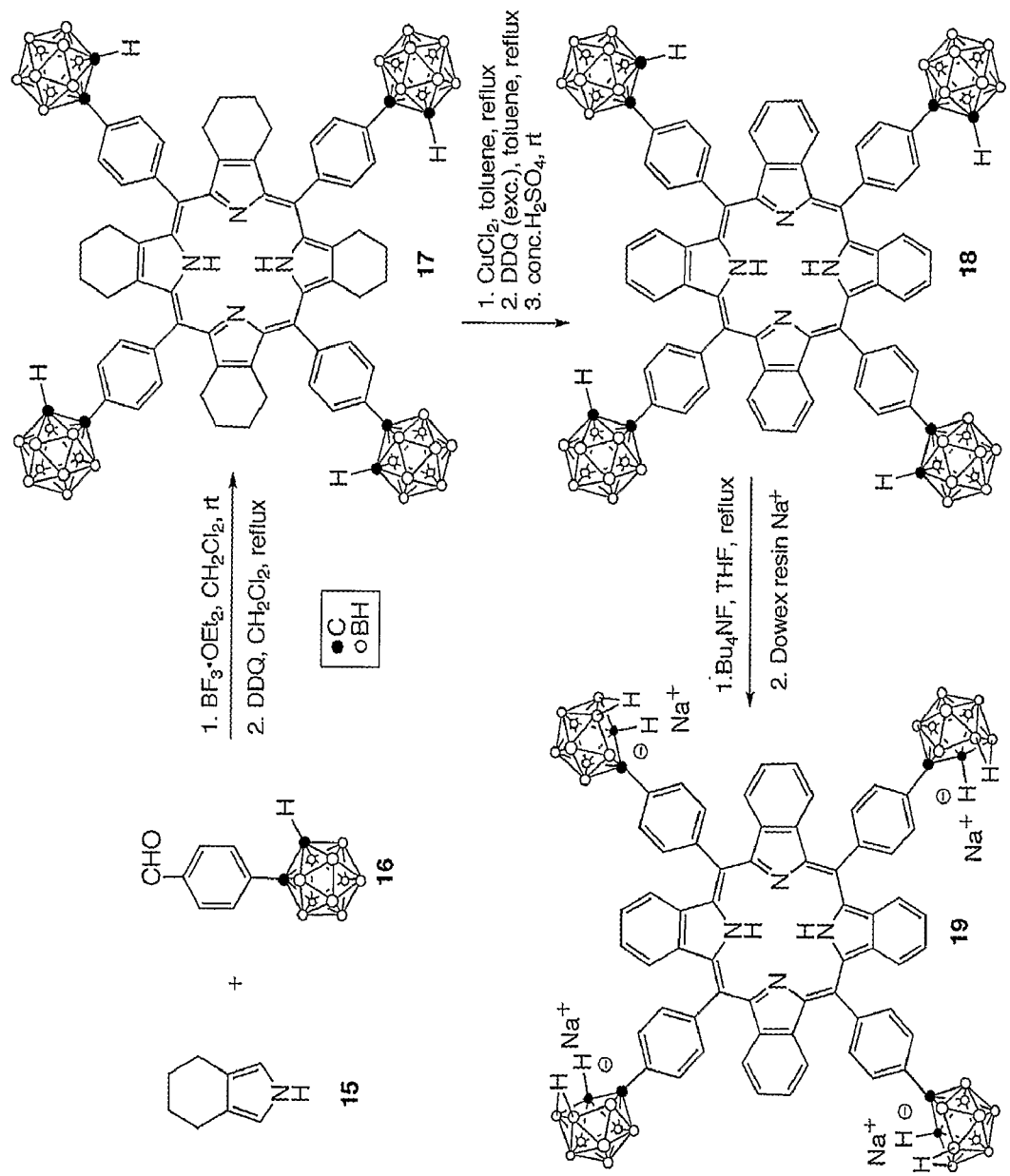
FIG. 9 depicts a reaction scheme leading to Compound 19.
Figure 10:
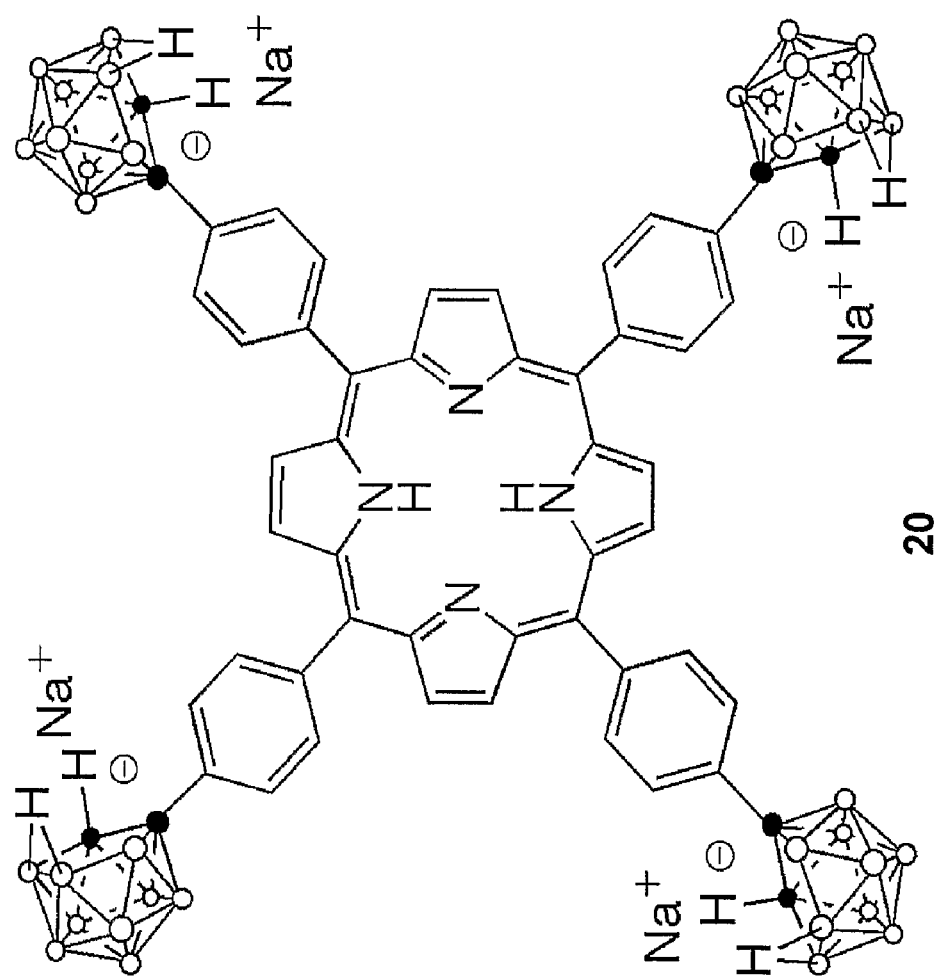
FIG. 10 depicts the structure of tetra(nido-carboranylphenyl)porphyrin 20.

Compound 13Cs (obtained by preparing Compound 13 in the presence of cesium carbonate) was easily converted into 13K or 13Na using Dowex™ ion-exchange resin in the K$^+$ or Na$^+$ form, respectively. Conjugates 13Cs, 13K, 13Na and Compound 5 were all highly soluble in the polar organic solvents acetone, ethyl acetate, acetonitrile, DMF, and DMSO. Interestingly, while Compound 13 was also soluble in methanol, compound 5 was not, and the only water soluble conjugates were 13K and 13Na. The fluorescence spectra of Compounds 13 and 5 (FIG. 8) showed emission peaks at 656 and 653 nm, respectively, in acetone solution upon excitation at 512 nm, indicating that they retained the characteristic fluorescence properties of porphyrin macrocycles.

EXAMPLE 13

Synthesis of Compound 17: 5,10,15,20-Tetra[4-(o-carboranyl)phenyl]-2:3,7:8,12:13, 17:18-butanoporphyrin 3:4-Butanopyrrole, Compound 15 (0.13 g, 1.06 mmol) and 4-(o-carboranyl)benzaldehyde, Compound 16 (0.26 g, 1.06 mmol) were dissolved in dried, freshly distilled dichloromethane. The solution was stirred at room temperature under argon for 15 minutes. The reaction flask was shielded from ambient light, and BF$_3$.OEt$_2$ (0.02 mL, 0.106 mmol) was added. This solution was stirred for 1 h at room temperature before DDQ (0.36 g, 1.59 mmol) was added. The final mixture was refluxed under argon for 1 h to give a dark green solution. After cooling to room temperature, the solvent was evaporated under vacuum, and the resulting residue was purified by column chromatography on alumina (grade III) using dichloromethane for elution. Recrystallization from methanol gave purple crystals of the Compound 17 (0.20 g, 60% yield), m. p.>300° C.; $^1$H NMR (CDCl$_3$, drop of d-TFA, 300 MHz): δ 8.36 (d, 8H, J=8.27 Hz, o-PhH), 8.03 (d, 8H, J=8.27 Hz, m-PhH), 4.33 (s, 4H, carborane-CH), 3.5-1.3 (br, 40H, BH), 2.55-2.40 (m, 8H, CH$_2$), 2.00-1.85 (m, 8H, CH$_2$), 1.80-1.65 (m, 8H, CH$_2$), 1.20-1.05 (m, 8H, CH$_2$), −0.47 (s, 4H, NH). UV-Vis (CH$_2$Cl$_2$): $\lambda_{max}$ (log ε) 466 (4.52), 617 (3.36), 674 (3.60) nm. HRMS (MALDI) m/z 1401.1681 (M+H$^+$), calculated for $C_{68}H_{94}N_4B_{40}$ 1401.1582.

EXAMPLE 14

Synthesis of Compound 18: 5,10,15,20-Tetra[4-(o-carboranyl)phenyl-tetrabenzoporphyrin To a solution of porphyrin 17 (150 mg, 0.11 mmol) in toluene (20 mL) was added an excess of copper(II) chloride (143 mg, 1.06 mmol). The mixture was refluxed about 2 h, until the reaction was complete as evidenced by TLC and UV-Vis spectrophotometry. The solvent was evaporated under vacuum, the residue dissolved in dichloromethane (150 mL) and washed once with aqueous saturated NaHCO$_3$, and once with water before being dried over anhydrous Na$_2$SO$_4$. After removal of the solvent under vacuum the remaining residue was purified by column chromatography on alumina (grade III) using dichloromethane for elution. The Cu(II)-porphyrin was recovered in quantitative yield by precipitation with dichloromethane/ethanol. To a solution of this Cu(II)-porphyrin (150 mg, 0.102 mmol) in toluene (20 mL) was added excess DDQ (185 mg, 0.82 mmol). The mixture was refluxed for 15 minutes. During reflux the color of the solution changed from red to deep green. The mixture was then cooled to room temperature, diluted with chloroform (150 mL), and washed once with aqueous saturated NaHCO$_3$ and once with water. The solvent was removed under vacuum, and the remaining residue was purified by column chromatography on alumina (grade III) using dichloromethane for elution. Recrystallization from methanol afforded Cu(II)-tetrabenzoporphyrin (110 mg, 75% yield) as dark green crystals. The Cu(II)-tetrabenzoporphyrin (110 mg, 0.076 mmol) was dissolved in concentrated sulfuric acid and stirred at room temperature for five minutes. The solution was poured into water/ice and extracted with chloroform (4×150 mL). The organic layers were collected, dried over anhydrous $Na_2SO_4$, and the solvent was evaporated under vacuum. The resulting residue was recrystallized from methanol to give green crystals of Compound 18 (105 mg) in quantitative yield from Cu(II)-tetrabenzoporphyrin. M. p.>300° C.; $^1$H NMR (acetone-$d_6$, 250 MHz): δ 8.34 (d, J=8.35 Hz, 8H, o-PhH), 8.17 (d, J=8.35 Hz, 8H, m-PhH), 7.49-6.93 (br m, 16H, benzoH), 5.55 (s, 4H, carborane-CH), 3.5-1.4 (br, 40H, BH), −1.04 (br s, 2H, NH). UV-Vis ($CH_2Cl_2$): $\lambda_{max}$ (log ε) 467 (10.10), 553 (3.80), 593 (4.00), 643 (4.37), 698 (3.90) nm. HRMS (MALDI) m/z 1385.0347 (M+H$^+$), calculated for $C_{68}H_{78}N_4B_{40}$ 1385.0326.

Although TBPs typically display low solubilities due to their planar π-conjugation systems and pronounced tendency for π-π stacking, TBP Compound 18 is soluble in organic solvents, such as dichloromethane and acetone, as a result of its non-planar structure and steric crowding about the macrocycle periphery. Compound 18 was converted to the water-soluble TBP Compound 19 with tert-butylammonium fluoride in THF, followed by cation exchange. TBP Compound 19 is highly soluble in polar organic solvents, such as acetone, methanol and DMSO, and is slightly soluble in water. Compounds 18 and 19 displayed absorption spectra characteristic of tetrabenzoporphyrins, with red-shifted bands compared with porphyrin 17.

EXAMPLE 15

Synthesis of Compound 19: 5,10,15,20-Tetra[4-(nido-carboranyl)phenyl-tetrabenzoporphyrin Tetrabenzoporphyrin 18 (25.0 mg, 0.018 mmol) was added to a 1 M solution of $Bu_4NF.3H_2O$ in THF (0.32 mL, 1.08 mmol), and the solution was refluxed for 6 h. After cooling to room temperature, the solvent was removed under vacuum, the residue was dissolved in dichloromethane and washed once with water before being dried over anhydrous $Na_2SO_4$. The solvent was evaporated under vacuum, the residue was re-dissolved in methanol and purified on a Sephadex™ LH-20 column, using methanol for elution. The resulting residue was dissolved in 40% aqueous acetone and passed slowly through a Dowex™ 50WX2-100 resin in sodium form. The porphyrin fraction was collected, dried under vacuum, re-dissolved in 60% aqueous acetone and passed twice through the ion-exchange resin. Removal of the solvent under vacuum gave the tetrabenzoporphyrin 19 (25.8 mg) in quantitative yield as a green powder. M. p.>300° C.; $^1$H NMR (acetone-$d_6$, 300 MHz): δ 8.04 (d, J=8.22 Hz, 8H, o-PhH), 7.82 (d, J=8.22 Hz, 8H, m-PhH), 7.48-7.28 (br m, 16H, benzoH), 2.69 (s, 4H, carborane-CH), 2.9-1.3 (br, 36H, BH), −1.13 (s, 2H, NH), −1.80-−2.25 (br s, 4H, BH). UV-Vis ($CH_2Cl_2$): $\lambda_{max}$ (log ε) 464 (5.2), 542 (3.73), 585 (3.97), 637 (4.27), 694 (3.60) nm. MS (MALDI-TOF) m/z 1433.619 (M+H$^+$). HPLC (water/acetonitrile): $t_r$=42.15 min.

EXAMPLE 16

Synthesis of Compound 21

5-(4-methoxyphenyl)-10,15,20-tri(4-hydroxyphenyl)porphyrin (23.5 mg, 0.034 mmol) and $K_2CO_3$ (280.0 mg, 2.0 mmol) were refluxed (60° C. oil bath) in 10 ml acetone in a 50 ml round-bottom flask under argon for 15 minutes. The reaction mixture was then cooled to room temperature, and compound 6 (60.0 mg, 0.15 mmol) was added. The reaction mixture was stirred at room temperature for two hours and refluxed overnight. The reaction mixture was then purified as otherwise described above for Compound 13. After washing with ether and vacuum drying at 50° C. for two days, Compound 21 (64.2 mg, 0.031 mmol) was obtained in 92.9% yield. HRMALDI-TOF-MS for $C_{69}H_{116}B_{54}N_4O_{10}Co_3K_3$: calc'd, 1992.1899 [M−3K+3Na+H]$^+$, found 1992.1954. LRMALDI-TOF-MS for $C_{69}H_{116}B_{54}N_4O_{10}Co_3K_3$: calc'd, 1992.166 [M−3K+3Na+H]$^+$, found 1992.184; calc'd, 2015.156 [M−3K+4Na+H]$^+$, found 2015.164. $^1$H-NMR (acetone-$d_6$): 8.90 (d, 2H, J=6.15 Hz, β-H), 8.13 (d, 2H, J=2.48 Hz, o-ArOCH$_3$—H), 8.09 (m, 6H, o-phenyl-H), 7.84 (m, 8H, m-phenyl-H), 4.37 (m, 12H, OCH$_2$), 4.30 (br, 3H, OCH$_3$), 4.06 (t, 6H, OCH$_2$), 4.01 (m, 6H, OCH$_2$), 3.74 (br, 12H, car-H), 1.6-3.0 (br, 51H, BH), −2.68 (s, 2H, NH). $^{13}$C NMR (acetone-$d_6$) 160.3, 136.6, 135.5, 121.1, 114.2, 113.5, 73.4, 70.8, 69.8, 69.0, 60.9 (OMe), 55.5, 47.7. UV-vis (acetone) $\lambda_{max}$ (nm) 419 (ε 593,100), 516 (23, 900), 553 (18,200), 593 (9, 100), 651 (8,900). HPLC $t_R$=11.04.

EXAMPLE 17

Synthesis of Compound 22

5-(3,5-hydroxyphenyl)-10,15,20-triphenyl porphyrin (32.3 mg, 0.05 mmol) and $K_2CO_3$ (28.5 mg, 0.21 mmol) were refluxed (60° C. oil bath) in 10 ml acetone in a 50 ml round-bottom flask under argon for 15 minutes. After cooling to room temperature, Compound 6 (41.2 mg, 0.1 mmol) was added. The mixture was stirred at room temperature for two hours, and then refluxed overnight, with another portion (11.5 mg) of Compound 6 added to drive the reaction to completion. The reaction mixture was then purified as otherwise described above for Compound 13. After washing with ether and vacuum drying at 50° C. for two days, Compound 22 (54.1 mg, 0.035 mmol) was obtained in 70.1% yield. This comparatively low yield is attributed to the slight solubility of the target compound in ether. Column chromatography on silica gel with a mixture of ethyl acetate and acetone gave a high yield of target compound (75.1 mg, 97.2% yield). MALDI-TOF-MS for $C_{60}H_{86}N_4O_6B_{36}Co_2K_2$: m/z calcd, 1545.556 [M+H]$^+$, found 1545.405; 1583.648 [M+K]$^+$, found 1583.533. $^1$H-NMR (acetone-$d_6$): 9.06 (d, 2H, β-H), 8.87 (m, 6H, β-H), 8.26 (m, 6H, o-phenyl-H), 7.84 (m, 9H, m,p-phenyl-H), 7.49 (d, 2H, o-Ar—H), 7.08 (d, 2H, p-Ar—H), 4.40 (t, 4H, OCH$_2$), 4.23 (t, 8H, OCH$_2$), 3.92 (t, 4H, OCH$_2$), 3.66 (s, 8H, car-H), 1.6-3.0 (br, 34H, BH), −2.76 (s, 2H, NH). $^{13}$C NMR (acetone-$d_6$) 159.1, 144.4, 142.8, 135.1, 128.6, 127.6, 120.8, 120.7, 115.3, 101.8, 72.8, 70.1, 69.1, 68.7, 54.7, 47.1. UV-vis (acetone) $\lambda_{max}$ (nm) 415 (ε 318,600), 511 (14,000), 544 (5,400), 589 (3,800), 646 (3,200). HPLC $t_R$=5.97.

EXAMPLE 18

Synthesis of Compound 23

5,15-di(3,5-hydroxyphenyl)-10,20-diphenyl porphyrin (34.2 mg, 0.05 mmol) and $K_2CO_3$ (54.9 mg, 0.40 mmol) were refluxed (60° C. oil bath) in 20 ml acetone in a 50 ml round-bottom flask under argon for 15 minutes. Then the reaction mixture was cooled to room temperature, and Compound 6 (82.2 mg, 0.20 mmol) was added to the reaction mixture. The reaction was then refluxed overnight, during which time another two portions (20.0 mg and 20.1 mg) of Compound 6 were added to drive the reaction to completion. The reaction mixture was then purified as otherwise described above for Compound 13. After washing with ether and vacuum drying, the target porphyrin 23 (111.4 mg, 0.045 mmol) was obtained in 89.8% yield. MALDI-TOF-MS for $C_{76}H_{142}N_4O_{12}B_{72}Co_4K_4$: calcd, 2410.944 [M−4K+4Na+H]$^+$, found 2410.985. $^1$H-NMR (acetone-$d_6$): 9.02 (d, 4H, β-H), 8.86 (d, 4H, β-H), 8.27 (m, 4H, o-phenyl-H), 7.84 (m, 6H, m,p-phenyl-H), 7.50 (s, 4H, o-Ar—H), 7.08 (s, 2H, p-Ar—H), 4.41 (t, 8H, OCH$_2$), 4.19 (s, 16H, OCH$_2$), 3.94 (t, 8H, OCH$_2$), 3.68 (s, 16H, car-H), 1.6-3.0 (br, 68H, BH), −2.77 (s, 2H, NH). $^{13}$C NMR (acetone-d$_6$) 159.1, 144.5, 142.7, 135.1, 128.6, 127.6, 120.8, 120.7, 115.2, 101.7, 72.8, 70.1, 69.1, 68.6, 54.4, 47.2. UV-vis (acetone) $\lambda_{max}$ (nm) 417 ($\epsilon$ 495,700), 512 (23,000), 546 (9,100), 588 (4,300), 645 (5,600). HPLC t$_R$=15.16.

EXAMPLE 19

Synthesis of Compound 24

5,10-di(3,5-hydroxyphenyl)-15,20-diphenyl porphyrin (17.2 mg, 0.025 mmol) and K$_2$CO$_3$ (28.1 mg, 0.20 mmol) were refluxed at 60° C. in 10 ml acetone in a 50 ml round-bottom flask under argon for 15 minutes. The reaction mixture was then cooled to room temperature and Compound 6 (60.3 mg, 0.15 mmol) was added to the reaction mixture. The reaction was then refluxed overnight, and two portions (11.0 mg and 10.3 mg) of Compound 6 were added to drive the reaction to completion. After washing with ether and vacuum drying, the target porphyrin 24 (57.1 mg, 0.023 mmol) was obtained in 91.3% yield. MALDI-TOF-MS for C$_{76}$H$_{142}$N$_4$O$_{12}$B$_{72}$Co$_4$K$_4$: calcd, 2410.944 [M−4K+4Na+H]$^+$, found 2410.553; calcd, 2432.926 [M−4K+5Na]$^+$, found 2433.100. $^1$H-NMR (acetone-d$_6$): 8.99 (s, 4H, β-H), 8.81 (d, 4H, β-H), 8.22 (m, 4H, o-phenyl-H), 7.80 (m, 6H, m,p-phenyl-H), 7.45 (d, 4H, o-Ar—H), 7.05 (s, 2H, p-Ar—H), 4.37 (t, 8H, OCH$_2$), 4.15 (s, 16H, OCH$_2$), 3.91 (t, 8H, OCH$_2$), 3.64 (s, 16H, car-H), 1.6-3.0 (br, 68H, BH), −2.81 (s, 2H, NH). $^{13}$C NMR (acetone-d$_6$) 159.1, 144.5, 142.7, 135.1, 128.6, 127.5, 120.9, 120.6, 115.2, 101.8, 72.9, 70.1, 69.1, 68.7, 54.4, 47.2. UV-vis (acetone) $\lambda_{max}$ (nm) 417 ($\epsilon$ 421,500), 512 (19,500), 546 (5,500), 588 (4,300), 645 (2,900). HPLC t$_R$=12.22.

EXAMPLE 20

Synthesis of Compound 25

5,10,15-tri(3,5-hydroxyphenyl)-20-phenyl porphyrin (11.8 mg, 0.017 mmol) and K$_2$CO$_3$ (28.0 mg, 0.20 mmol) were refluxed at 60° C. in 10 ml acetone in a 50 ml round-bottom flask under argon for 15 minutes. The reaction mixture was then cooled to room temperature, and Compound 6 (42.0 mg, 0.10 mmol) was added. The reaction was then refluxed overnight, and two portions of Compound 6, totaling 21.0 mg, were added to drive the reaction to completion. After washing with ether and vacuum drying overnight, the target porphyrin 25 (52.8 mg, 0.016 mmol) was obtained in 93.4% yield. MALDI-TOF-MS for C$_{92}$H$_{198}$N$_4$O$_{18}$B$_{108}$Co$_6$K$_6$: calcd, 3405.212 [M+H]$^+$, found 3405.342; calcd, 3428.202 [M+Na$^+$H]$^+$, found 3428.271; calcd, 3444.312 [M+K$^+$H]$^+$, found 3445.391. $^1$H-NMR (acetone-d$_6$): 9.00 (s, 6H, β-H), 8.85 (d, 2H, β-H), 8.26 (m, 2H, o-phenyl-H), 7.84 (m, 3H, m,p-phenyl-H), 7.48 (s, 6H, o-Ar—H), 7.08 (s, 3H, p-Ar—H), 4.40 (t, 12H, OCH$_2$), 4.18 (s, 24H, OCH$_2$), 3.94 (t, 12H, OCH$_2$), 3.68 (s, 24H, car-H), 1.6-3.0 (br, 102H, BH), −2.81 (s, 2H, NH). $^{13}$C NMR (acetone-d$_6$) 159.1, 144.5, 142.7, 135.1, 128.6, 127.5, 120.9, 120.6, 115.2, 101.8, 72.9, 70.1, 69.1, 68.7, 54.4, 47.2. UV-vis (acetone) $\lambda_{max}$ (nm) 418 ($\epsilon$ 396,100), 512 (19,500), 546 (7,400), 588 (7,200), 644 (4,700). HPLC t$_R$=11.61.

EXAMPLE 21

Synthesis of Compound 26

5,10,15,20-tetra(3,5-hydroxyphenyl) porphyrin (18.9 mg, 0.025 mmol) and K$_2$CO$_3$ (500.0 mg, 3.62 mmol) were refluxed (60° C. oil bath) in 20 ml acetone in a 50 ml round-bottom flask under argon for 15 minutes. The reaction mixture was cooled to room temperature, and Compound 6 (100.0 mg, 0.25 mmol) was added and refluxed overnight, with two portions (40 mg and 21 mg) of Compound 6 added to drive the reaction to completion. After washing with ether and drying under vacuum, the target porphyrin 21 (104.2 mg, 0.024 mmol) was obtained in 94.5% yield. MALDI-TOF-MS for C$_{108}$H$_{254}$N$_4$O$_{24}$B$_{144}$Co$_8$K$_8$: m/z calcd, 4335.040 [M+H]$^+$, found 4335.507; 4374.140 [M+H+K]$^+$, found 4374.678. $^1$H-NMR (acetone-d$_6$): 8.99 (s, 8H, β-H), 7.45 (s, 8H, o-Ar—H), 7.08 (s, 4H, p-phenyl-H), 4.39 (t, 16H, OCH$_2$), 4.21 (br, 32H, OCH$_2$), 3.93 (t, 16H, OCH$_2$), 3.68 (s, 32H, car-H), 1.6-3.0 (br, 136H, BH), −2.82 (s, 2H, NH). $^{13}$C NMR (acetone-d$_6$) 159.5, 144.9, 121.0, 115.6, 102.3, 73.2, 70.6, 70.2, 69.6, 55.0, 47.6. UV-vis (acetone) $\lambda_{max}$ (nm) 419 ($\epsilon$ 425,200), 512 (21,700), 546 (7,200), 587 (7,200), 645 (4,000). HPLC t$_R$=5.66.

EXAMPLES 22 AND 23

Synthesis of Compounds 27 and 28

5-(4-aminophenyl)-5,10,15-triphenylporphyrin (33.0 mg, 0.05 mmol) and Compound 6 (41.0 mg, 0.1 mmol) were added to a mixture of 2.5 ml CHCl$_3$ and 5 ml CH$_3$CN. The mixture was refluxed overnight, and the reaction mixture was separated on a silica gel column using chloroform and ethyl acetate mixture solvents, yielding two major fractions 27 and 28. Both fractions were recrystallized from chloroform/hexane and dried under vacuum.

Compound 27: (25.7 mg, 0.024 mmol), yield 46%. HRM-ALDI-TOF-MS for C$_{52}$H$_{59}$N$_5$O$_2$B$_{18}$Co$_2$Na: calcd, 1063.5794 [M+H]$^+$, found 1063.5802; calcd 1039.5818 [M−Na]$^-$, found 1039.5863. $^1$H-NMR (acetone-d$_6$): 9.02 (d, 2H, β-H), 8.83 (m, 6H, β-H), 8.22 (m, 6H, o-phenyl-H), 7.95 (d, 2H, o-Ar—H), 7.81 (m, 9H, m,p-phenyl-H), 7.07 (d, 2H, p-Ar—H), 5.23 (b, 1H, NH), 4.38 (s, 2H, OCH$_2$), 4.31 (s, 2H, OCH$_2$), 3.83 (t, 2H, OCH$_2$), 3.66 (m, 4H, car-H), 3.50 (t, 2H, NCH$_2$), 1.6-3.0 (br, 17H, BH), −2.67 (s, 2H, NH). $^{13}$C NMR (acetone-d$_6$) 149.6, 142.9, 142.8, 136.4, 135.1, 130.3, 128.6, 127.6, 122.7, 120.7, 120.2, 111.8, 72.6, 70.2, 69.2, 55.3, 47.2, 44.2. UV-vis (acetone) $\lambda_{max}$ (nm) 415 ($\epsilon$ 242,200), 515 (15,900), 555 (11,600), 589 (6,600), 651 (5,600). HPLC (method b) t$_R$=4.20.

Compound 28: (20.4 mg, 0.014 mmol), yield 26%. HRM-ALDI-TOF-MS for C$_{60}$H$_{87}$N$_5$O$_4$B$_{36}$Co$_2$Na$_2$: calcd, 1498.8910 [M+H]$^+$, found 1496.9001; calcd, 1472.8933 [M−Na]$^-$, found 1472.8957. $^1$H-NMR (acetone-d$_6$): 9.08 (d, 2H, β-H), 8.84 (m, 6H, β-H), 8.23 (m, 6H, o-phenyl-H), 8.08 (d, 2H, o-Ar—H), 7.80 (m, 9H, m,p-phenyl-H), 7.26 (d, 2H, p-Ar—H), 4.42 (b, 4H, OCH$_2$), 4.30 (b, 8H, OCH$_2$), 3.90 (b, 8H, OCH$_2$), 3.70 (b, 8H, car-H), 1.6-3.0 (br, 34H, BH), −2.60 (s, 2H, NH). $^{13}$C NMR (acetone-d$_6$) 148.6, 142.7, 136.5, 135.0, 134.9, 129.5, 128.4, 127.4, 122.6, 120.5, 120.0, 111.1, 72.7, 69.0, 68.9, 55.3, 51.6, 47.0. UV-vis (acetone) $\lambda_{max}$ (nm) 413 ($\epsilon$ 222,600), 516 (15,800), 559 (13,000), 591 (7,900), 651 (6,300). HPLC t$_R$=13.93. HPLC (method b) t$_R$=5.29.

EXAMPLES 24 AND 25

Synthesis of N-Substituted Porphyrins 29 and 30

H$_2$TPP (61.4 mg, 0.10 mmol) and 65.4 mg (0.16 mmol) of Compound 6 were added to 25 ml ODCB. The reaction mixture was stirred at 140° C., and it turned green in about 15 minutes. After two hours, TLC indicated that all H$_2$TPP had been consumed, and the reaction was stopped. The reaction mixture was then loaded directly onto a silica gel column using toluene to elute ODCB and any residual H$_2$TPP. Compound 29 was then eluted by DCM, and Compound 30 was eluted by a mixture of DCM and acetone. Both fractions were recrystallized from chloroform/hexane and dried under vacuum.

Compound 29: (82.8 mg, 0.081 mmol), yield 80.8%. HRMALDI-TOF-MS for $C_{52}H_{59}N_4O_2B_{18}Co$: calcd, 1025.5788, found 1025.5717. $^1$H-NMR (CDCl$_3$): 9.32 (d, 2H, J=5.0 Hz, β-H), 9.08 (d, 2H, J=5.0 Hz, β-H), 8.85 (s, 2H, β-H), 8.54 (b, 4H, o-phenyl-H), 8.32 (d, 2H, J=7.75, o-phenyl-H), 8.23 (d, 2H, J=7.75, o-phenyl-H), 8.15 (s, 2H, β-H), 8.00 (m, 6H, m, p-phenyl-H), 7.87 (m, 6H, m, p-phenyl-H), 3.91 (s, 2H, car-H), 3.30 (s, 2H, car-H), 3.07 (t, 2H, OCH$_2$), 2.71 (t, 2H, OCH$_2$), 0.71 (t, 2H, OCH$_2$), 0.1-4.0 (br, 17H, BH), −4.83 (t, 2H, NCH$_2$). UV-Vis (CH$_2$Cl$_2$) $\lambda_{max}$ (nm) 450 (ε 320,500), 613 (13, 800), 669 (38,300).

Compound 30: (6.8 mg, 0.005 mmol), yield 4.7%. HRMALDI-TOF-MS for $C_{60}H_{87}N_4O_4B_{36}Co_2Na$: calcd, 1458.8903, found 1458.8850, calcd, 1481.8801 [M+Na]$^+$, found 1481.8874; calcd, 1435.9006 [M−Na]$^−$, found 1435.9014. $^1$H-NMR (acetone-d$_6$): 8.97 (d, 2H, J=4.9 Hz, β-H), 8.79 (m, 4H, β-H), 8.53 (b, 2H, o-phenyl-H), 8.33 (m, 4H, o-phenyl-H), 8.17 (t, 2H, o-phenyl-H), 8.01 (m, 9H, m, p-phenyl-H), 7.91 (m, 3H, m, p-phenyl-H), 7.77 (d, 2H, J=4.7, β-H), 4.24 (s, 8H, OCH$_2$), 3.48 (m, 8H, car-H), 1.16 (t, 2H, OCH$_2$), 0.08 (t, 2H, OCH$_2$), 0.1-4.0 (br, 34H, BH), −2.64 (s, 1H, NH), −4.30 (m, 2H, NCH$_2$), −5.83 (m, 2H, NCH$_2$). UV-Vis (CH$_2$Cl$_2$) $\lambda_{max}$ (nm) 465 (ε 285,950), 696 (58,250).

EXAMPLE 26

Synthesis of N-cobaltacarborane Octaethylporphyrin 31

2,3,7,8,12,13,17,18-octaethyl-porphyrin (53.5 mg, 0.10 mmol) (OEP) and [3,3'-Co(8-C$_4$H$_8$O$_2$-1,2-C$_2$B$_9$H$_{10}$ (1',2'-C$_2$B$_9$H$_{10}$)] (43.3 mg, 0.11 mmol) were dissolved in 10 mL of ODCB. The reaction solution was stirred at 140° C. for 2 hours until TLC indicated no OEP remained. The reaction mixture was purified on a silica gel column using dichloromethane/hexane for elution. The first, purple fraction was collected and recrystallized from chloroform/hexane and dried under vacuum to yield the porphyrin 31 (86.1 mg, 89%). HRMALDI-TOF-MS for $C_{44}H_{75}N_4O_2B_{18}CoNa$: calcd, 968.6934 [M+Na]$^+$, found 968.6957. $^1$H-NMR (CDCl$_3$): 10.67 (s, 2H, meso-H), 10.41 (d, 2H, meso-H), 4.28-4.42 (m, 8H, CH$_2$), 4.18-4.22 (m, 2H, car-H), 4.04-4.15 (m, 8H, CH$_2$), 3.59 (brs, 2H, car-H), 3.02-3.05 (m, 2H, OCH$_2$), 2.27-2.30 (m, 2H, OCH$_2$), 1.96-2.01 (t, 12H, CH$_3$), 1.47-1.53 (t, 12H, CH$_3$), 0.09-0.22 (m, 2H, OCH$_2$), 0.1-4.0 (br, 17H, BH), −5.60--5.57 (m, 2H, NCH$_2$). UV-Vis (Acetone) $\lambda_{max}$ (nm) 400 (ε 145, 500), 539 (9, 200), 562 (12, 400), 581 (10, 200).

EXAMPLE 27

Synthesis of N,N-dicobaltacarborane Octaethylporphyrin 32

Mono-substituted porphyrin 31 (48.5 mg, 0.05 mmol), [3,3'-Co(8-C$_4$H$_8$O$_2$-1,2-C$_2$B$_9$H$_{10}$(1',2'-C$_2$B$_9$H$_{10}$)] (30.5 mg, 0.075 mmol) and NaHCO$_3$ (42.3 mg, 0.5 mmol) were stirred with 10 mL of ODCB. Then the reaction mixture was heated at 140° C. until complete disappearance of porphyrin 31 from TLC. The reaction mixture was purified on a silica gel column using dichloromethane/ethyl acetate for elution. The main fraction was collected and recrystallized from chloroform/hexane and dried under vacuum to yield porphyrin 32 (26.6 mg, 73.%). HRMALDI-TOF-MS for $C_{52}H_{103}N_4O_2B_{36}Co_4Na_2$: calcd, 1401.0078 [M+Na]$^+$, found 1401.0092. $^1$H-NMR (Acetone-d$^6$): 11.38 (s, 1H, meso-H), 11.33 (s, 2H, meso-H), 11.09 (s, 1H, meso-H), 3.93-4.36 (m, 16H, CH$_2$), 3.81 (brs, 4H, car-H), 3.38 (brs, 4H, car-H), 2.85 (m, 4H, OCH$_2$), 2.36 (brs, 4H, OCH$_2$), 1.85-1.88 (m, 12H, CH$_3$), 1.44-1.56 (m, 6H, CH$_3$), 1.27-1.42 (m, 6H, CH$_3$), 0.12 (brs, 4H, OCH$_2$), 0.1-4.0 (br, 34H, BH), −5.41--5.35 (m, 2H, NCH$_2$), −6.44-6.38 (m, 2H, NCH$_2$). UV-Vis (Acetone) $\lambda_{max}$ (nm) 427 (ε 141, 500), 573 (9, 800), 617 (5, 300).

EXAMPLE 28

Synthesis of Porphyrin 33

Porphyrin 33 was prepared from tetra(4-hydroxyphenyl) porphyrin and compound 6 in a manner similar to that described for Example 16. The corresponding tert-butyl protected conjugate 5 was obtained in 91% yield, m.p.=262-265° C. (dec). HPLC $t_r$=12.52 min. UV-Vis (acetone) $\lambda_{max}$ (ε/M$^-$$_1$cm$^{-1}$) 419 (396 700), 516 (26 000), 552 (21 200), 593 (8 600), 650 (9 000). $^1$H-NMR (acetone-d$_6$, 250 MHz): δ 8.90-8.93 (m, 8H, βH), 8.13 (d, 8H, J=7.9 Hz, o-PhH), 7.36-7.43 (d, 8H, J=8.5 Hz, m-PhH), 4.92 (s, 2H, CH$_2$), 4.50 (s, 6H, OCH$_2$), 4.33 (s, 6H, OCH$_2$), 4.28 (s, 6H, OCH$_2$), 4.04 (s, 6H, OCH$_2$), 3.75 (s, 12H, carborane-H), 1.6-3.0 (br, 51H, BH), 1.59 (s, 9H, CH$_3$), −2.70 (s, 2H, NH). $^{13}$C-NMR (acetone-d$_6$, 63 MHz): δ 168.5, 159.7, 158.9, 136.1, 135.5, 134.9, 131.8, 120.6, 120.2, 113.7, 82.1, 72.8, 70.2, 69.2, 68.5, 66.3, 65.8, 61.6, 54.8, 47.1, 28.1. LRMS (MALDI-TOF) m/z 2139.003 (M$^+$), calculated for $C_{74}H_{124}N_4O_{12}B_{54}Co_3K_3$ 2139.602. To a solution of this conjugate (100 mg, 0.0467 mmol) in chloroform (5 mL) was added TFA (5 mL). The mixture was stirred at room temperature for 4 h. Solvent was removed under vacuum, and the residue was triturated with 5 mL of Et$_2$O. The resulting green precipitate was washed with Et$_2$O (6×10 mL) to remove residual TFA, and dried under vacuum to give 93 mg, 95% yield, of pure conjugate 5, m.p.=283-285° C. (dec). HPLC $t_r$=16.59 min. UV-Vis (acetone) λmax (ε/M$^-$$_1$cm$^{-1}$) UV-Vis (acetone) $\lambda_{max}$ (ε/M$^{-1}$cm$^{-1}$) 419 (408 000), 516 (17 800), 553 (14 250), 593 (8 300), 650 (8 800). $^1$H-NMR (acetone-d$_6$, TFA): δ 8.78 (br, 8H, β-H), 8.48 (br, 8H, o-PhH), 7.64 (br, 8H, m-PhH), 5.10 (s, 2H, CH$_2$), 4.53 (s, 6H, OCH$_2$), 4.36 (s, 6H, OCH$_2$), 4.29 (s, 6H, OCH$_2$), 4.05-4.06 (m, 6H, OCH$_2$), 3.73 (s, 12H, carborane-H), 0.77-2.43 (br, 51H, BH). LRMS (MALDI-TOF) m/z 2083.518 (M+H$^+$), calculated for $C_{70}H_{116}N_4O_{12}B_{54}Co_3K_3$ 2083.498.

EXAMPLE 29

Cell Culture Studies

Human glioblastoma T98G cells and cervical carcinoma HEp2 cells were obtained from ATCC. Both cell lines were maintained in 50% α-MEM/advanced MEM, supplemented with 5% fetal bovine serum. Phosphate buffered saline (PBS), fetal bovine serum, and trypsin were purchased from Gibco; Cyquant reagent and Lysosensor were purchased from Molecular Probes, and Triton X-100 was purchased from Calbiochem. Microscopy was performed on a Zeiss Axiovert 200M inverted fluorescence microscope fitted with standard Texas Red and FITC filter sets (Chroma Technology Corp.). Images were acquired with a Zeiss Axiocam MRM CCD camera fitted to the microscope, and were pseudo-colored with Adobe Photoshop® CS version 8.0. Compounds 19 and 20 were dissolved in DMSO (Sigma-Aldrich) prior to being diluted into cell medium so that the final DMSO concentration never exceeded 1%. All medium solutions were filter-sterilized (22 μm pore size) prior to use. All data obtained in the FLUOstar plate reader was analyzed using Prism 3.0 graphing software.

EXAMPLES 30 AND 31

Concentration-dependent Cellular Uptake

Human T98G cells were sub-cultured on 96-well plates at 10,000 cells/100 μL α-MEM/advanced medium per well, and were incubated for 48 h. A 200 µM stock solution of TBP in DMSO was diluted with α-MEM/advanced medium, and was added to the cells to achieve final concentrations for TBP Compound 19 of 200, 100, 50, 25, 12.5, 6.25, 3.125, and 0 µM. After incubation for 3 h the medium was removed, the cells were washed with PBS, and 100 µL of 0.25% Triton X-100 in PBS was added to each well. A TBP Compound 19 standard fluorescence graph was obtained by diluting a 10 µM stock solution in 0.25% Triton X-100 in PBS to achieve 10, 5, 2.5, 1.25, 0.625, 0.3125 and 0 µM TBP concentrations. Fluorescence of the TBP Compound 19 at the different dilutions was then measured on a FLUOstar plate reader using 570 nm excitation and 720 nm emission filters. A standard curve for different cell numbers was obtained by placing 100,000, 80,000, 60,000, 40,000, 20,000, 10,000, and 0 cells in the wells, followed by incubation for 3 h. A standard graph was prepared from the wells with known cell numbers. Unknown cell numbers from the experiments were determined by first adding 100 µL/well of 5 µM stock solution of Cyquant reagent in PBS, and then reading the plate on a FLUOstar plate reader using 480 nm excitation and 520 emission filters. The same procedure was followed for determining the concentration-dependent cellular uptake of porphyrin 20, but using 570 nm excitation and 650 nm emission filters.

Figure 11:
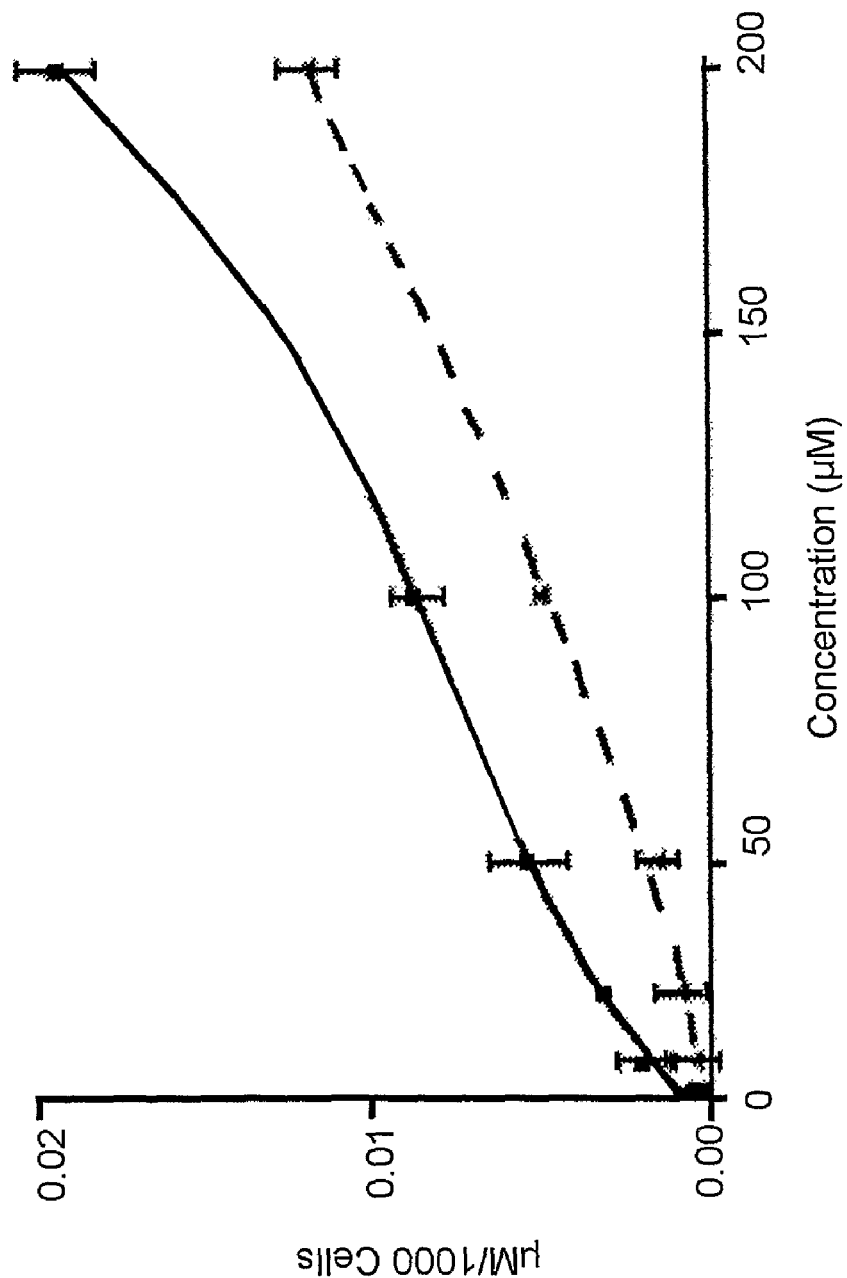
FIG. 11 depicts the concentration-dependent uptake of TBP 5 (full line) and porphyrin 6 (dotted line) by human glioma T98G cells, after a 3-hour exposure.

As shown in FIG. 11, the uptake of Compounds 19 and 20 increased with increasing concentration, in an almost linear fashion. TBP 19 accumulated within cells to a concentration approximately 30% higher than did porphyrin 20. This difference may be a result of the higher hydrophobicity of TBP 19 compared with 20, resulting from the presence of the four β,β'-fused benzene rings.

EXAMPLES 32 AND 33

Time-dependent Cellular Uptake

Human T98G cells were sub-cultured and incubated for 48 h as otherwise described above. A filter-sterilized, 10 µM stock solution of TBP 19 in 1% DMSO/medium was added, and the cells were incubated for 24, 16, 8, 4, 2, 1, 0.5 and 0 h. The medium was removed, the cells were washed with PBS, and 100 µL of 0.25% Triton X-100 in PBS was added to each well. Known and unknown concentrations of TBP 19 were determined as described above for the concentration-dependent uptake. The same procedure was followed to monitor time-dependent uptake of porphyrin 20.

Figure 12:
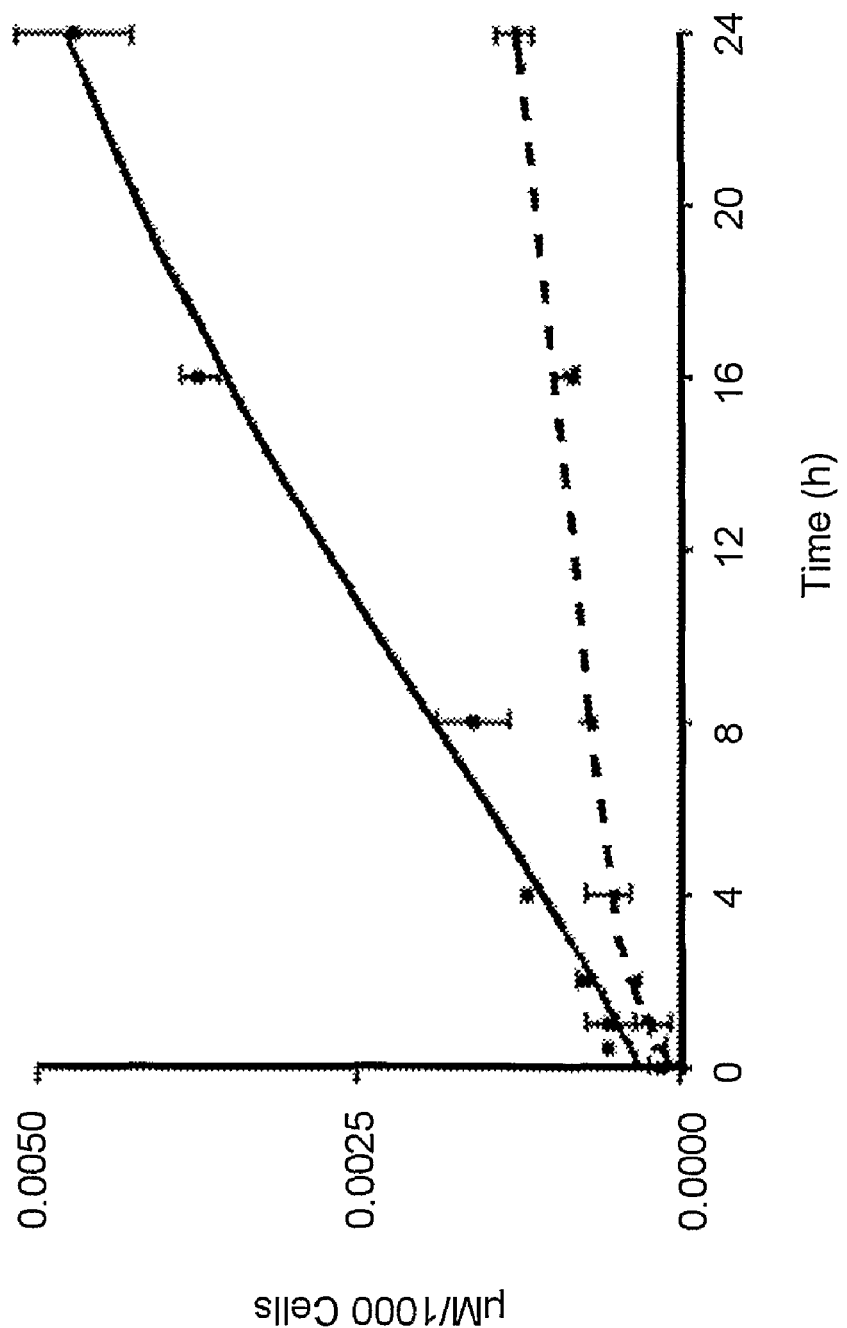
FIG. 12 depicts the time-dependent uptake of TBP 5 (full line) and porphyrin 6 (dashed line) at 10 μM by human glioma T98G cells.
Figure 13:
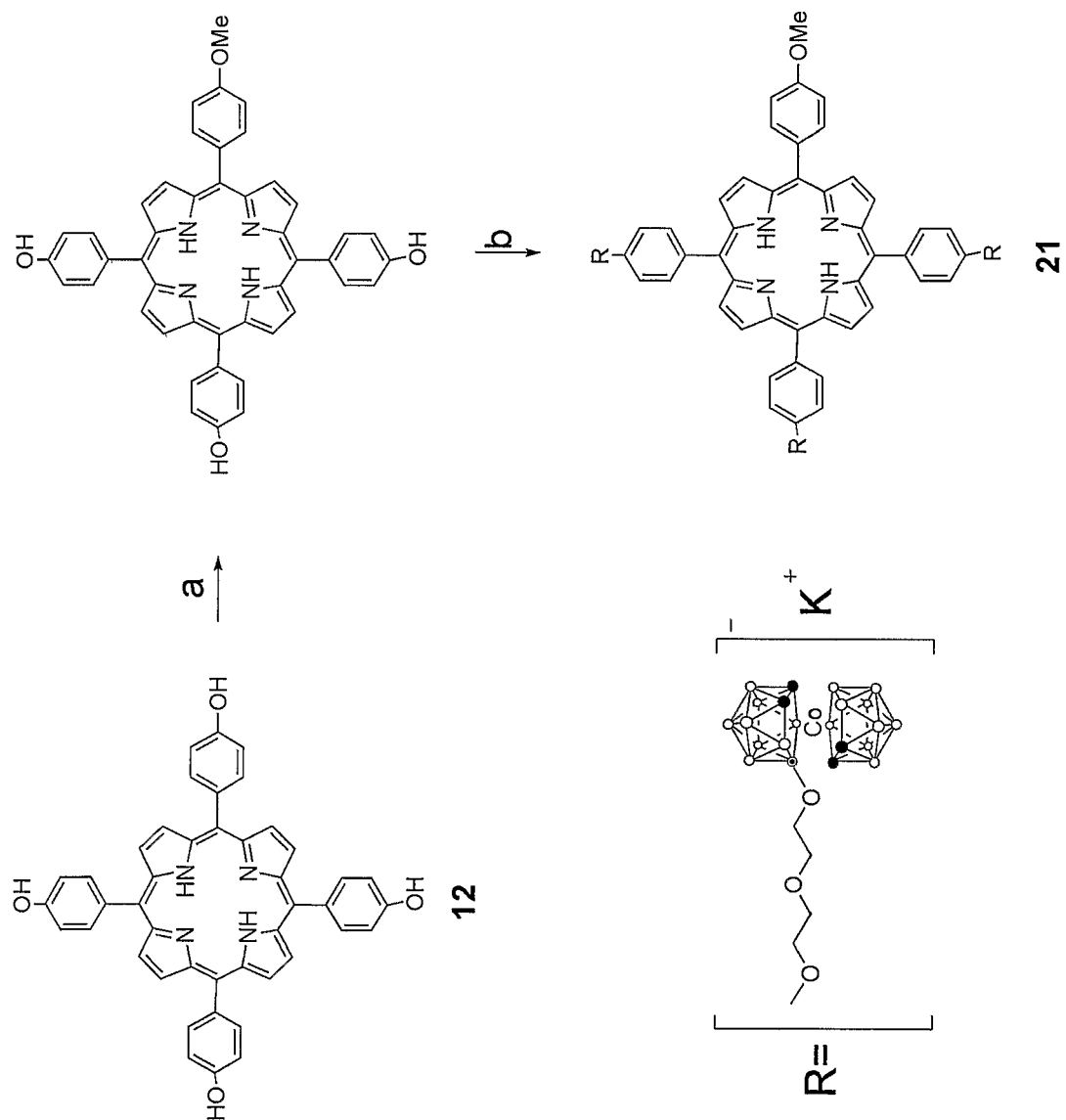
FIG. 13 depicts the synthesis of Compound 21: (a) MeI, $K_2CO_3$, DMSO; (b) Compound 6, $K_2CO_3$, Acetone.
Figure 14:
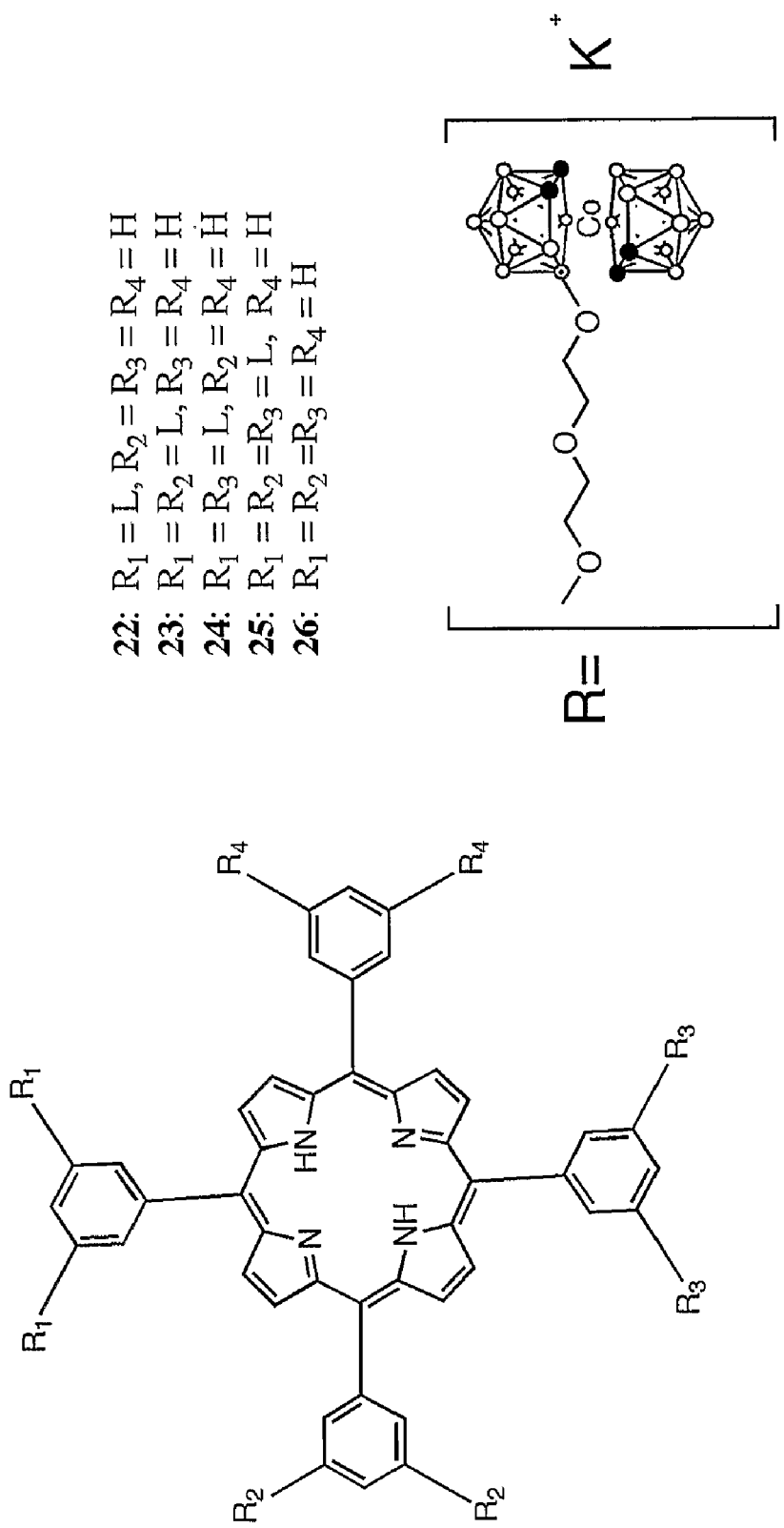
FIG. 14 depicts Compounds 22-26.
Figure 15:
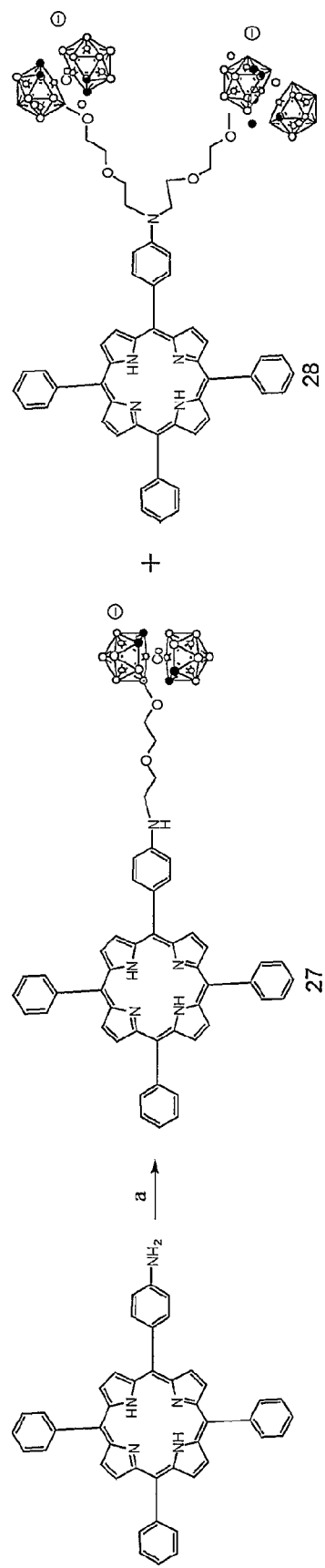
FIG. 15 depicts Compounds 27 and 28.
Figure 16:
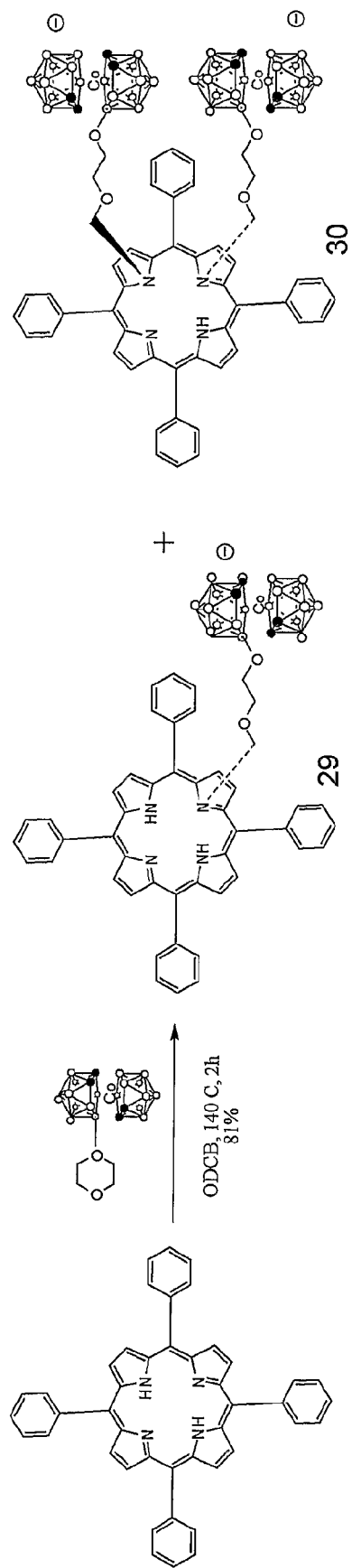
FIG. 16 depicts Compounds 29 and 30.
Figure 17:
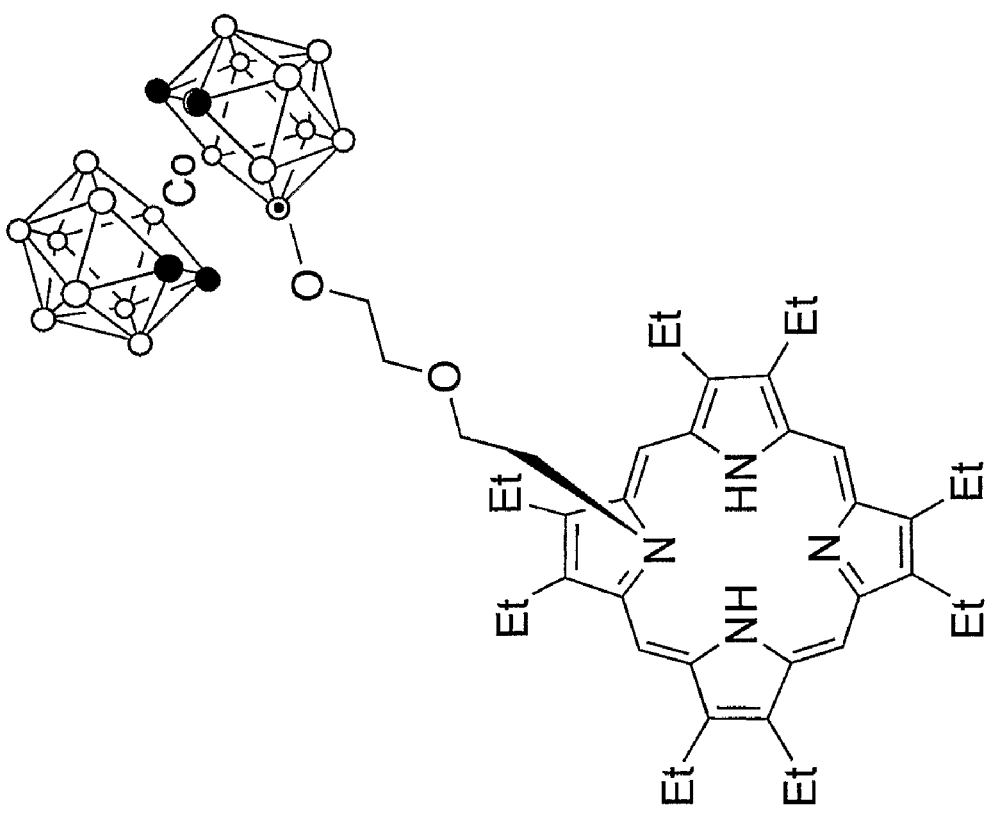
FIG. 17 depicts Compound 31.
Figure 18:
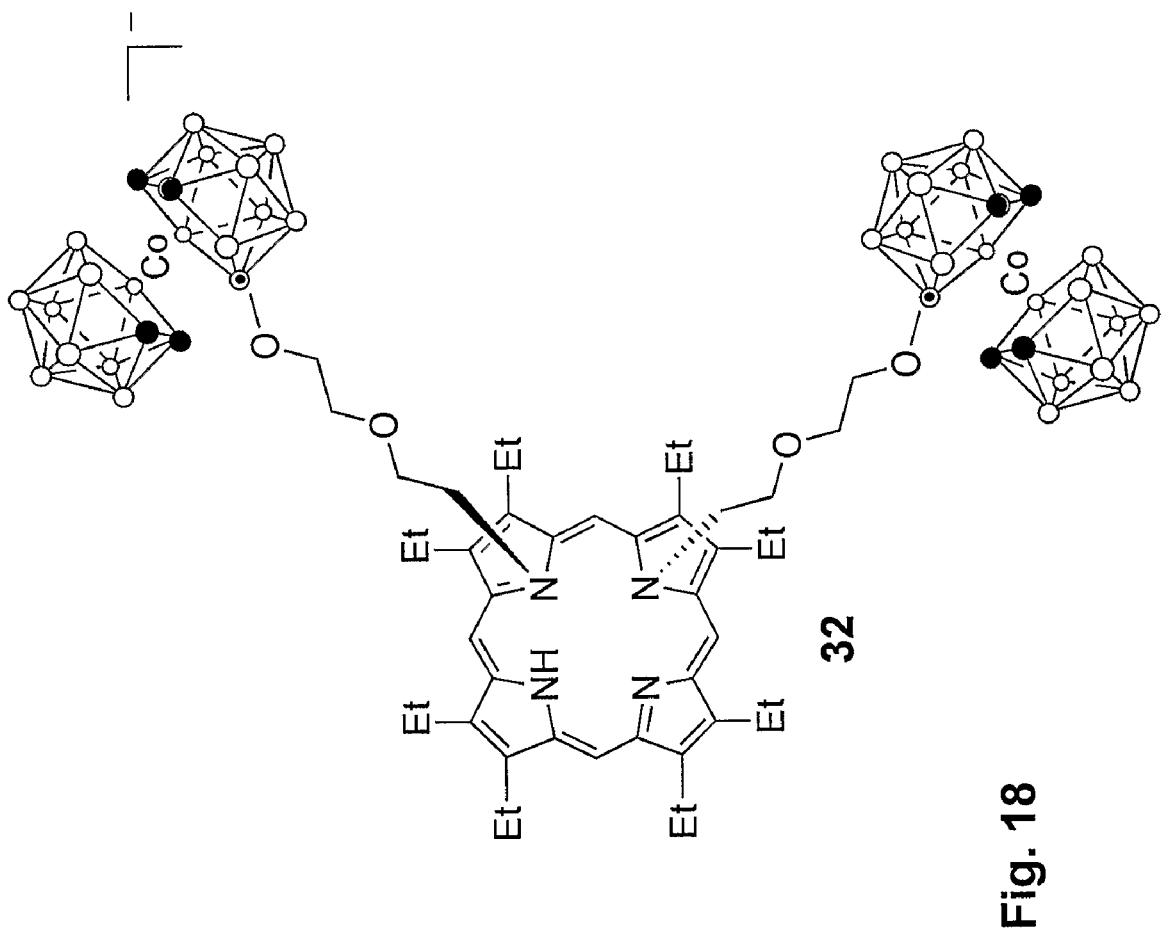
FIG. 18 depicts Compound 32.
Figure 19:
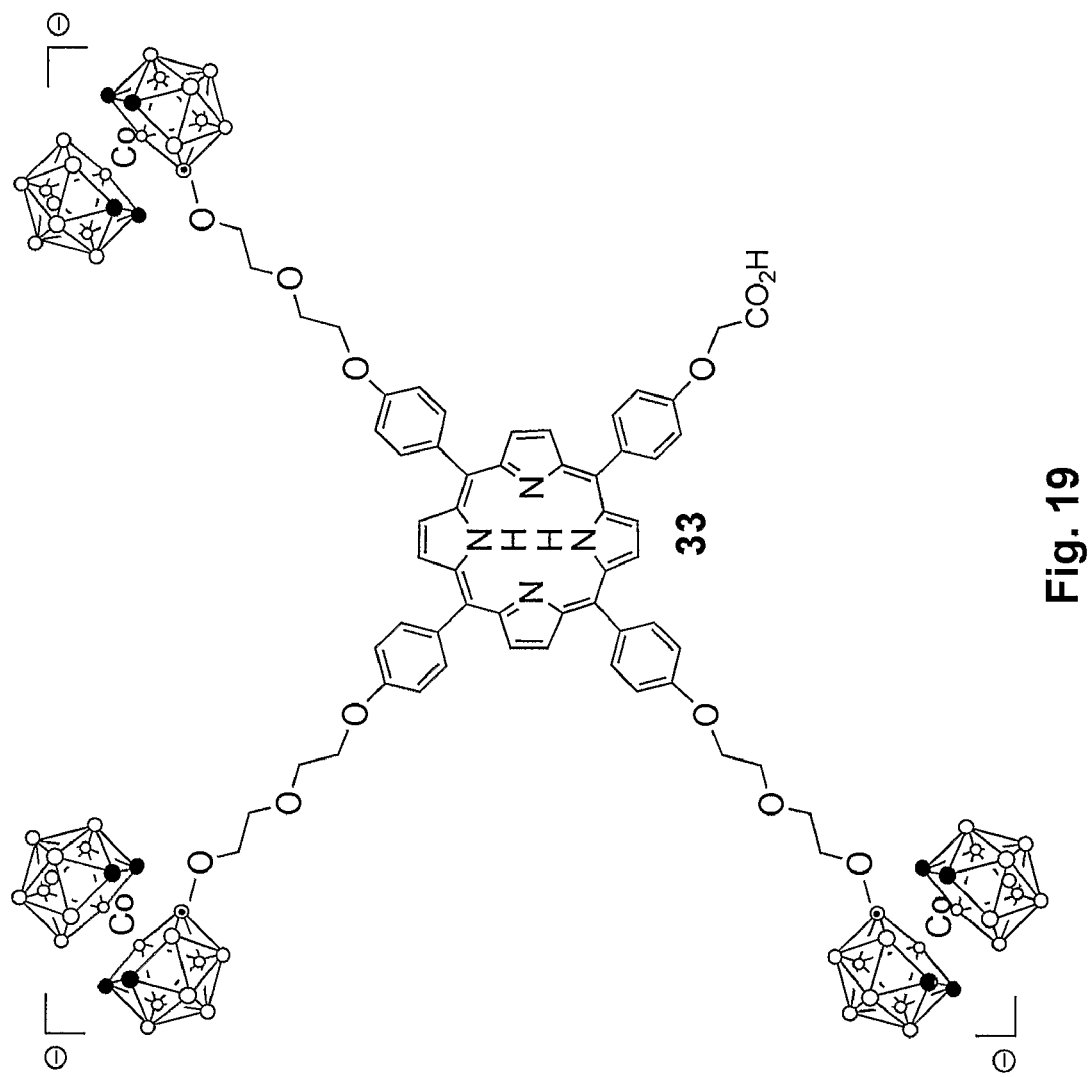
FIG. 19 depicts Compound 33.
Figure 20:
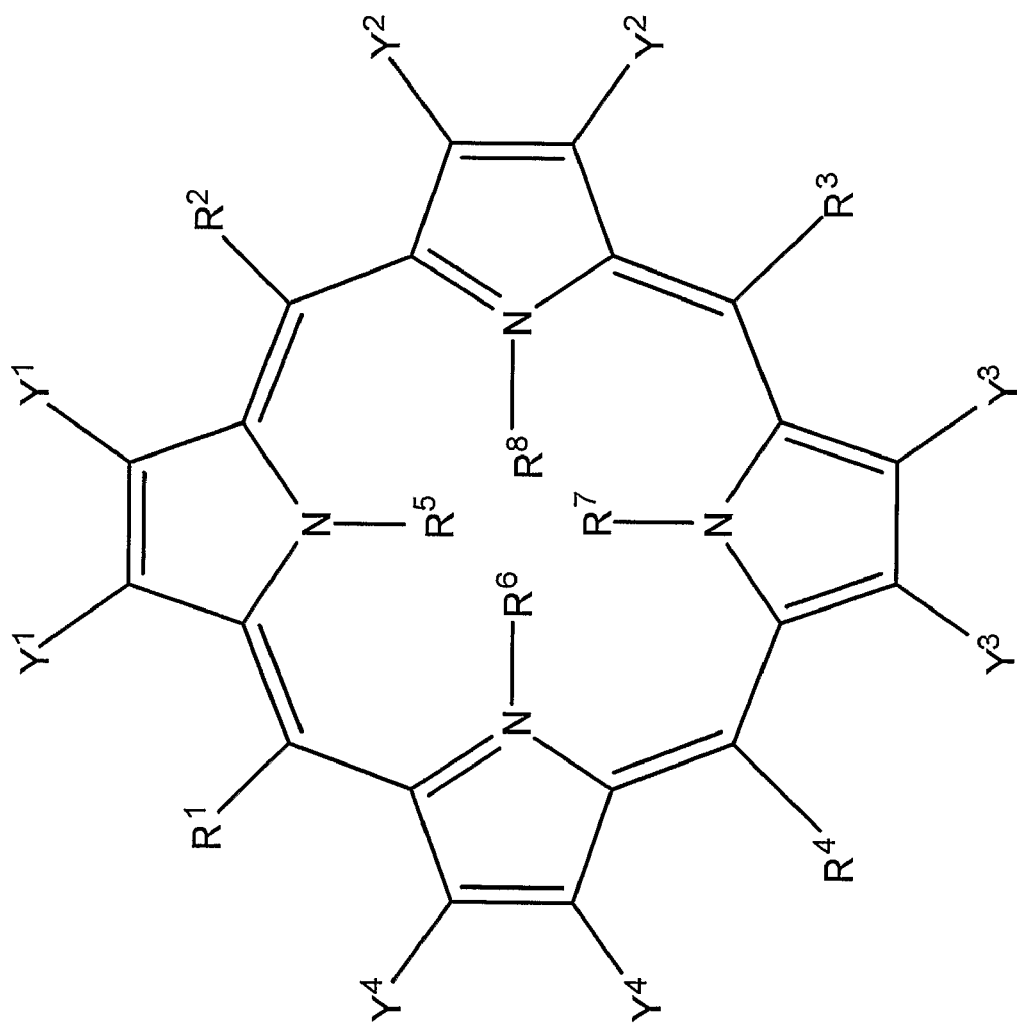
FIG. 20 depicts a generic version of Compounds within the scope of this invention.

The time-dependent cellular uptake of compounds 19 and 20 is shown in FIG. 12. TBP 19 was taken up faster and to a greater extent than porphyrin 20 at all times; for example, after 24 h there was approximately 3 times more Compound 19 than Compound 20 within T98G cells.

EXAMPLES 34 AND 35

Intracellular Localization

Human HEp2 cells were sub-cultured on Lab-Tek II chamber cover slips with α-MEM/advanced medium for 48 h. TBP 5 was added to each chamber to reach a final concentration of 50 µM. The cells were incubated for 24 h, washed twice with 50 mM HEPES to remove unbound TBP. New medium containing 50 mM HEPES pH 7.4 was added, and the cells were examined immediately by fluorescence microscopy. For the co-localization experiments 100 nM of Lysosensor was added to the TBP-containing cells 30 minutes before completion of the incubation period.

The punctate fluorescence pattern observed for TBP 19 (not shown) was very similar to that seen for Lysosensor, and was consistent with localization in the cellular lysosomes. An overlay between TBP 19 and Lysosensor fluorescence images (not shown) confirmed that the two compounds co-localized in the lysosomes.

EXAMPLES 36-39

Animal Toxicity

Balb/c male and female mice were injected intraperitoneally (i.p.) with Compounds 19, 20, or vehicle control. The maximum dosage administered (groups 9 and 10) was 160 mg/kg, and represented a maximum saturation of 4 mg/mL. No serum chemistry changes were observed that were attributable either to the experimental Compounds or to vehicle administration, as shown in the clinical and histological values given in Tables 1-4.

Twelve groups of two BALB/c mice each, 4-6 weeks of age and weighing 12-24 g (mean=19 g), were used for toxicity studies. There were 8 female and 16 male mice. Mice in groups 1, 3, 5, 7, and 9 were administered TBP 19 once via i.p. injection, at increasing dosages: group 1 (20 mg/kg of a 2 mg/ml solution), group 3 (40 mg/kg of a 2 mg/ml solution), group 5 (80 mg/kg of a 4 mg/ml solution), group 7 (120 mg/kg of a 4 mg/ml solution), and group 9 (160 mg/kg of a 4 mg/ml solution). Mice in groups 2, 4, 6, 8, and 10 were administered porphyrin 20 once via i.p. injection at increasing dosages: group 2 (20 mg/kg of a 2 mg/ml solution), group 4 (40 mg/kg of a 2 mg/ml solution), group 6 (80 mg/kg of a 4 mg/ml solution), group 8 (120 mg/kg of a 4 mg/ml solution), and group 10 (160 mg/kg of a 4 mg/ml solution). Two groups of mice served as vehicle controls. Mice in group 11 received sterile 4% Cremophor EL (Fluka) in PBS and served as controls for mice receiving 20, 40, and 80 mg/kg compound; while mice in group 12 received 6% Cremophor EL and served as controls for mice receiving 120 and 160 mg/kg compound.

For each compound, groups were dosed sequentially and each group was evaluated daily for signs of toxicity, including hunched posture, rough hair coat, and decreased responsiveness. Mice were anesthetized with $CO_2$ 48 h after compound administration, and blood was collected by cardiocentesis for clinical chemistry evaluation. Serum chemistry was analyzed, including glucose, aspartate aminotransferase (AST), alanine aminotransferase (ALT), alkaline phosphatase (AP), bilirubin, total protein (TP), albumin, globulin, and blood urea nitrogen (BUN). The mice were exsanguinated and necropsies were performed. Tissues, including lung, kidney, thymus, heart, Harderian gland, spleen, stomach, small intestine and colon were fixed in 10% neutral buffered formalin. The fixed tissues were processed and examined by a board-certified pathologist.

No signs of toxicity were observed in any mice injected either with TBP 19 (Tables 1 and 2) or with porphyrin 20 (Tables 3 and 4). With both compounds, increased glucose levels were attributed to excitement and increased corticosteroid release. The serum AST levels were all similar, and although generally higher than normal for some mice, were not considered elevated due to administration of Compound 19 or 20, or vehicle administration, because the observed increases were inconsistent. These results suggest that muscle injury or exertion may have contributed to increased AST levels in some mice. The serum ALT levels were also similar, and although higher than normal in some mice, were not considered elevated due to administration of Compound 19 or 20, or vehicle administration, because the elevations were not consistent among mice in the same treatment groups. Furthermore, serum ALT is not specific for hepatocellular injury in mice. The serum AP levels differed by group, but were all within the normal range, as were the serum bilirubin levels. The serum TP levels differed by group, but were generally within the normal range. The serum albumin levels for mice in group 9 (who were administered Compound 19) were lower than for other mice; this observation may be due to decreased synthesis resulting from hepatocellular injury, or increased loss through renal or intestinal disease. However, tissue injury was not evident histopathologically. Likewise, the serum globulin levels were lower than expected, or lower than for control mice in groups 1, 3, and 9. These findings likely represented a stress response, rather than compound or vehicle effects. The serum BUN levels differed among groups, but were also within normal limits. Extramedullary hematopoiesis was observed in all mice, and may represent mild levels of stress, typical of mice under manipulative experimental conditions.

The non-toxicity of TBP 19 and porphyrin 20 up to a dose of 160 mg/kg is in agreement with the low toxicity that has been reported for hydrophobic carboranylporphyrins. These preliminary results suggest that Compounds 19 and 20 were significantly less toxic than other negatively charged carboranyl-containing porphyrins, such as BOPP, MnBOPP, BTPP, NiNTCP-H, ZnDPE and NiDPE. The novel nido-carboranylporphyrins had low toxicities in mice, even at high doses.

Tables 1 and 2 summarize clinical data obtained in mice injected with TBP 19, while Tables 3 and 4 summarize results obtained for mice injected with porphyrin 20.

Table 1 presents serum chemistry values for six BALB/c mice administered TBP 5 (groups 1, 3, 5) or 4% Cremophore (vehicle: group 11), by i.p. injection. The values represent mean (SEM) serum chemistry levels. For individual analytes measured, entries in a single row having superscripts in common were not significantly different from one another ($p>0.05$).

TABLE 1

| Group | 1 | 3 | 5 | 11 |
|---|---|---|---|---|
| Glucose | $153.5^a$ | $219.5^c$ | $229.5^c$ | $188.0^b$ |
| AST | 177.5 | 455.5 | 454.5 | 83.0 |
| ALT | 151.5 | 96.5 | 120.0 | 31.0 |
| AP | $189.5^{a,c}$ | $201.0^{b,c}$ | $138.0^a$ | $128.5^a$ |
| Bilirubin | 0.15 | 0.20 | 0.20 | 0.15 |
| Total Prot. | 4.65 | 4.7 | 5.1 | 4.5 |
| Albumin | 2.85 | 2.8 | 2.75 | 2.75 |
| Globulin | $1.8^a$ | $1.9^a$ | $2.35^b$ | $2.3^b$ |
| BUN | 28.0 | 27.0 | 25.5 | 29.0 |

Table 2 presents serum chemistry values for four BALB/c mice administered TBP 5 (groups 7, 9) or 6% Cremophore (vehicle: group 12), by i.p. injection. The values represent mean (SEM) serum chemistry levels. For individual analytes measured, entries in a single row having superscripts in common were not significantly different from one another ($p>0.05$).

TABLE 2

| Group | 7 | 9 | 12 |
|---|---|---|---|
| Glucose | 224.5 | 172.0 | 206.5 |
| AST | 73.0 | 498.0 | 774.0 |
| ALT | 29.0 | 206.0 | 411.5 |
| AP | $161.0^a$ | $223.5^b$ | $169.0^c$ |
| Bilirubin | 0.2 | 0.25 | 0.2 |
| Total Prot. | $5.1^a$ | $4.35^b$ | $4.65^b$ |
| Albumin | $2.75^a$ | $2.4^b$ | $2.6^c$ |
| Globulin | $2.35^a$ | $1.95^b$ | $2.05^b$ |
| BUN | $15.5^{a,b}$ | $22.5^{b,c}$ | $33.0^c$ |

Table 3 presents serum chemistry values for six BALB/c mice administered porphyrin 6 (groups 2, 4, 6) or 4% Cremophore (vehicle: group 11), by i.p. injection. The values represent mean (SEM) serum chemistry levels. For individual analytes measured, entries in a single row having superscripts in common were not significantly different from one another ($p>0.05$).

TABLE 3

| Group | 2 | 4 | 6 | 11 |
|---|---|---|---|---|
| Glucose | $159.5^a$ | $188.0^b$ | $153.5^a$ | $188.0^b$ |
| AST | 146.0 | 202.0 | 258.0 | 83.0 |
| ALT | 98.5 | 94.0 | 340.0 | 31.0 |
| AP | $167.5^a$ | $132.0^{a,c}$ | $148.0^{a,c}$ | $128.5^{b,c}$ |
| Bilirubin | 0.2 | 0.25 | 0.25 | 0.15 |
| Total Prot. | $4.3^a$ | $4.6^{a,b}$ | $5.0^b$ | $4.5^b$ |
| Albumin | 2.7 | 2.6 | 2.8 | 2.75 |
| Globulin | $1.6^a$ | $2.0^b$ | $2.35^c$ | $2.3^c$ |
| BUN | 26.5 | 24.0 | 27.5 | 29.0 |

Table 4 presents serum chemistry values for four BALB/c mice administered porphyrin 6 (groups 8, 10) or 6% Cremophore (vehicle: group 12), by i.p. injection. The values represent mean (SEM) serum chemistry levels. For individual analytes measured, entries in a single row having superscripts in common were not significantly different from one another ($p>0.05$).

TABLE 4

| Group | 8 | 10 | 12 |
|---|---|---|---|
| Glucose | 239.5 | 214.5 | 206.5 |
| AST | 774.0 | 981.0 | 774.0 |
| ALT | 968.0 | 1096.0 | 411.5 |
| AP | $160.5^a$ | $223.0^b$ | $169.0^a$ |
| Bilirubin | 0.25 | 0.25 | 0.2 |
| Total Prot. | 4.9 | 4.5 | 4.65 |
| Albumin | 2.5 | 2.5 | 2.6 |
| Globulin | $2.4^a$ | $2.0^b$ | $2.05^{a,b}$ |
| BUN | $16.0^a$ | $25.5^{a,b}$ | $33.0^b$ |

MISCELLANEOUS

Compounds used in the present invention may be administered to a patient for treatment of cancers, macular disease, and other clinical treatments where selective destruction of tissue is desired, by any suitable means, including oral, intravenous, parenteral, subcutaneous, intrapulmonary, and intranasal administration. Parenteral infusions include intramuscular, intravenous, intraarterial, or intraperitoneal administration. The compounds may also be administered transdermally, for example in the form of a slow-release subcutaneous implant, or orally in the form of capsules, powders, or granules, with or without a coating such as an enteric coating. They may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampoule, each containing a unit dose amount, or in the form of a container containing multiple doses.

A compound in accordance with the present invention may be formulated into therapeutic compositions as pharmaceutically acceptable salts. These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

A method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

Following administration of the compound, photodynamic therapy, boron neutron capture therapy, or both may be conducted using techniques otherwise known in the art.

Initial in vivo animal trials to demonstrate effectiveness against tumors will be conducted in accordance with all applicable laws and regulations, following by clinical trials in humans in accordance with all applicable laws and regulations.

As used in the specification and claims, an "effective amount" of a compound is an amount, that when administered to a patient (whether as a single dose or as a time course of treatment), in conjunction with PDT or BNCT where indicated, inhibits or reduces the growth of targeted tissues (e.g., tumors) to a clinically significant degree; or alternatively, to a statistically significant degree as compared to control. "Statistical significance" means significance at the $P<0.05$ level, or such other measure of statistical significance as would be used by those of skill in the art of biomedical statistics in the context of a particular type of treatment or prophylaxis.

The complete disclosures of all references cited throughout the specification are hereby incorporated by reference, as is the complete disclosure of the priority provisional application, U.S. provisional patent application Ser. No. 60/730,331, filed 25 Oct. 2005. Also incorporated by reference are the complete disclosures of the following references by, or attributable in pertinent part to, the inventor: V. Gottumukkala, R. Luguya, F. R. Fronczek and M. G. H. Vicente. Synthesis and Cellular Studies of an Octa-anionic 5,10,15,20-Tetra[3,5-(nido-carboranylmethyl)phenyl]porphyrin ($H_2OCP$) for Application in BNCT. *Bioorganic and Medicinal Chemistry* 2005, 13 (5), 1633-1640; E. Hao and M. G. H. Vicente. Expeditious Synthesis of Porphyrin-cobaltacarborane Conjugates. *Chemical Communications* 2005, 1306-1308; O. Ongayi, V. Gottumukkala, F. R. Fronczek and M. G. H. Vicente. Synthesis and Characterization of a Carboranyl-tetrabenzoporphyrin. *Bioorganic and Medicinal Chemistry Letters* 2005, 15(6), 1665-1668; J. C. Clark, F. R. Fronczek and M. G. H. Vicente. Novel □-Carboranylporphyrins for Application in Boron Neutron Capture Therapy (BNCT) of Tumors. *Tetrahedron Letters* 2005, 46, 2365-2368; S. Kawabata, R. F. Barth, W. Yang, G. Wu, V. Gottumukkala and M. G. H. Vicente. Evaluation of Carboranylporphyrins as Potential Delivery Agents for Neutron Capture Therapy of Brain Tumors. *Proceedings of the American Association for Cancer Research*, 2005, 46, 1122; S. Kawabata, R. F. Barth, W. Yang, G. Wu, P. J. Binns, K. J. Riley, V. Gottumukkala and M. G. H. Vicente. Evaluation of the Carboranylporphyrin H2TCP as a Delivery Agent for Boron Neutron Capture Therapy (BNCT). *Proceedings of the 13th World Congress of Neurological Surgery* 2005, 975-979; R. J. Luguya, F. R. Fronczek, K. M. Smith and M. G. H. Vicente. Carboranylcorroles. *Tetrahedron Letters* 2005, 46(32), 5365-5368; E. Hao, T. J. Jensen, B. H. Courtney and M. G. H. Vicente. Synthesis and Cellular Studies of Porphyrin-Cobaltacarborane Conjugates. *Bioconjugate Chemistry* 2005, 16, 1495-1502; V. Gottumukkala, O. Ongayi, D. G. Baker, L. G. Lomax and M. G. H. Vicente. Synthesis, Cellular Uptake and Animal Toxicity of a Tetra (carboranylphenyl)-tetrabenzoporphyrin. *Biorganic and Medicinal Chemistry* 2006, 14(6), 1871-1879; M. Sibrian-Vazquez, E. Hao, T. J. Jensen and M. G. H. Vicente. Enhanced Cellular Uptake with a Cobaltacarborane-Porphyrin-HIV-1 Tat 48-60 Conjugate. *Bioconjugate Chemistry* 2006, 17, 928-934; R. Luguya, T. J. Jensen, K. M. Smith and M. G. H. Vicente. Synthesis and Cellular Studies of a Carboranylchlorin for the PDT and BNCT of Tumors. *Bioorganic and Medicinal Chemistry* 2006, 14, 5890-5897; M. G. H. Vicente and M. W. Easson. Syntheses of Phosphonate- and Amine-substituted Carboranylporphyrins for Boron Neutron Capture Therapy of Tumors. *Proceedings for the 12th International Symposium on Neutron Capture Therapy for Cancer* 2006, 231-233; and S. Kawabata, R. F. Barth, W. Yang, G. Wu, P. J. Binns, K. J. Riley, O. Ongayi, V. Gottumukkala and M. G. H. Vicente. Evaluation of Carboranylporphyrins as Boron Delivery Agents for Neutron Capture Therapy. *Proceedings for the 12th International Symposium on Neutron Capture Therapy for Cancer* 2006, 123-126; M. G. H. Vicente. A. Wickramasinghe, S. Shetty and K. M. Smith. New Carbon-Carbon Linked Amphiphilic Carboranyl-Porphyrins as Boron Neutron Capture Agents. *Proceedings for the Ninth International Symposium on Neutron Capture Therapy for Cancer* 2000, 121-122; B. Edwards, K. Matthews, Y. Hou, M. G. H. Vicente, S. Autry-Conwell and J. Boggan. In Vitro and In Vivo Analyses of Boronated Porphyrins. *Proceedings for the Ninth International Symposium on Neutron Capture Therapy for Cancer* 2000, 61-62; M. G. H. Vicente, D. J. Nurco, S. J. Shetty, C. J. Medforth and K. M. Smith. First Structural Characterization of a Covalent Bonded Porphyrin-Carborane System. *Chemical Communications* 2001, 483-484; R. Lauceri, R. Purrello, S. J. Shetty and M. G. H. Vicente. Interactions of Anionic Carboranylated Porphyrins with DNA. *Journal of the American Chemical Society* 2001, 123, 5835-5836; M. G. H. Vicente. Porphyrin-based Sensitizers in the Detection and Treatment of Cancer: Recent Progress. *Current Medicinal Chemistry, Anti-Cancer Agents* 2001, 1, 175-194; S. Chayer, L. Jaquinod, K. M. Smith and M. G. H. Vicente. Syntheses of Carboranylpyrroles. *Tetrahedron Letters* 2001, 42, 7759-7761; M. G. H. Vicente, B. F. Edwards, S. J. Shetty, Y. Hou and J. E. Boggan. Synthesis and Preliminary Biological Studies of Four Tetra(nido-carboranylmethylphenyl)porphyrins. *Bioorganic and Medicinal Chemistry* 2002, 10, 481-492; A. Maderna, R. Huertas, M. F. Hawthorne, R. Luguya and M. G. H. Vicente. Synthesis of a Porphyrin-Labelled Carboranyl Phosphate Diester: A Potential New Drug for Boron Neutron Capture Therapy of Cancer. *Chemical Communications* 2002, 1784-1785; J. Osterloh and M. G. H. Vicente. Mechanisms of Porphyrinoid Localization in Tumors. *Journal of Porphyrins and Phthalocyanines* 2002, 6, 305-324; M. G. H. Vicente, D. J. Nurco, S. J. Shetty, J. Osterloh, E. Ventre, V. Hegde and W. A. Deustch. Synthesis, Dark Toxicity and Induction of in vitro DNA Photodamage by a Tetra(4-nido-carboranylphenyl)porphyrin. *Journal of Photochemistry and Photobiology B: Biology* 2002, 68, 123-132; M. G. H. Vicente, A. Wickramasighe, D. J. Nurco, H. J. H. Wang, M. M. Nawrocky, M. S. Makar and M. Miura. Syntheses, Toxicity and Biodistribution of two 5,15-Di[3,5-(nido-carboranylmethyl)phenyl]porphyrin in EMT-6 Tumor Bearing Mice. *Bioorganic and Medicinal Chemistry* 2003, 11, 3101-3108; B. Fabre, S. Chayer and M. G. H. Vicente. First conducting Polymer Functionalized with Covalently Linked Carborane Units. *Electrochemistry Communications* 2003, 5, 431-434; R. Luguya, L. Jaquinod, F. Fronczek, K. M. Smith and M. G. H. Vicente. Synthesis and Reactions of meso-(p-Nitrophenyl)porphyrins. *Tetrahedron* 2004, 60 (12), 2757-2763; R. Luguya, F. R. Fronczek, K. M. Smith and M. G. H. Vicente. Synthesis of Novel Carboranylchlorins with Dual Application in Boron Neutron Capture Therapy (BNCT) and Photodynamic Therapy (PDT). *Journal of Applied Radiation and Isotopes* 2004, 61(5), 1117-1123; M. G. H. Vicente, V. Gottumukkala, A. Wickramasinghe, M. Anikovsky and M. A. J. Rodgers. Singlet Oxygen Generation and Dark Toxicity of a nido- and a closo-Carboranylporphyrin. *Proceedings of SPIE, The International Society for Optical Engineering* 2004, 5315, 33-40; P. Bobadova-Parvanova, Y. Oku, A. Wickramasinghe, R. W. Hall and M. G. H. Vicente. Ab initio and $^1$H-NMR Study of the Zn(II) Complexes of a nido- and a closo-Carboranylporphyrin. *Journal of Porphyrins and Phthalocyanines* 2004, 8, 996-1006; W. Liu, M. R. Kumar, M. G. H. Vicente, F. R. Fronczek and K. M. Smith. New Water-soluble Phthalocyanines and other Tetrapyrroles for Application in Photodynamic Therapy. *Proceedings of SPIE, The International Society for Optical Engineering* 2005, 5689, 39-47; R. F. Barth, J. A. Coderre, M. G. H. Vicente and T. E Blue. Boron Neutron Capture Therapy of Cancer: Current Status and Future Prospects. *Clinical Cancer Research* 2005, 11, 3987-4002; J. C. Clark, B. Fabre, F. R. Fronczek and M. G. H. Vicente. Syntheses and Properties of Carboranylpyrroles. *Journal of Porphyrins and Phthalocyanines* 2005, 9, 803-810; E. Hao, F. R. Fronczek and M. G. H. Vicente. Oxacalixarene-Locked Bis-porphyrins and Higher Oligomers. *Journal of Organic Chemistry* 2006, 71, 1233-1236; M. W. Renner, M. Miura, M. W. Easson and M. G. H. Vicente. Recent Progress in the Syntheses and Biological Evaluation of Boronated Porphyrins for BNCT. *Current Medicinal Chemistry—Anti-Cancer Agents* 2006, 6(2), 145-158; B. Fabre, J. C. Clark and M. G. H. Vicente. Synthesis and Electrochemistry of Carboranylpyrroles. Toward the Preparation of Electrochemically and Thermally Resistant Conjugated Polymers. *Macromolecules* 2006, 39. 112-119. In the event of an otherwise irreconcilable conflict, however, the present specification shall control.

What is claimed:

1. A compound having the structure:

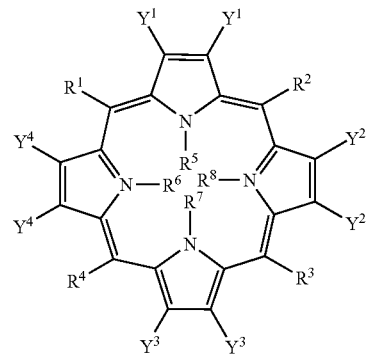

wherein:
the $R^1$-$R^4$ groups are the same or different, and each is selected from the group consisting of hydrogen, phenyl, hydroxyphenyl, $(C_2B_9H_{11})$phenyl, $(C_2B_{10}H_{11})$phenyl, pyridyl, substituted pyridyl, and metallobisdicarboillides;
the Groups $R^5$, $R^6$, $R^7$ and $R^8$ are the same or different, and are selected from the group consisting of hydrogen, metal atoms, and $(CH_2CH_2O)_2[Co(C_2B_9H_{11})_2]$; and
the two $Y^1$ groups are the same, the two $Y^2$ groups are the same, the two $Y^3$ groups are the same, and the two $Y^4$ groups are the same; wherein the several groups $Y^1$, $Y^2$, $Y^3$ and $Y^4$ may be the same or different from one another; and wherein the groups $Y^1$, $Y^2$, $Y^3$ and $Y^4$ are each selected from the group consisting of hydrogen, —CH=CH—, methyl, ethyl, propyl, isopropyl, and butyl; and wherein if, the two $Y^n$ groups are —CH=CH—, wherein n is 1, 2, 3 or 4, then those two $Y^n$ groups are bonded together to form the group —CH=CH—CH=CH—, so that the compound thereby contains a fused benzene ring at the $Y^n$ positions; and
at least one of $Y^1$, $Y^2$, $Y^3$, $Y^4$, $R^1$, $R^2$, $R^3$, and $R^4$ is not hydrogen.

2. A compound as recited in claim 1, wherein at least one of the groups $R^5$, $R^6$, $R^7$ and $R^8$ is $(CH_2CH_2O)_2[Co(C_2B_9H_{11})_2]$.

3. A compound as recited in claim 1, wherein the groups $R^5$, $R^6$, $R^7$ and $R^8$ are, collectively, a metal atom.

4. A compound as recited in claim 1, wherein the groups $R^5$, $R^6$, $R^7$ and $R^8$ are, collectively, a metal atom selected from the group consisting of Zn(II), Cu(II), Ni(II), Pd(II), Al(III), Sn(IV), Ga(III), Si(IV), Ge(IV), In(III), and Gd(III).

5. A compound as recited in claim 1, wherein at least one of the groups $R^1$, $R^2$, $R^3$ and $R^4$ is $(CH_2CH_2O)_2[Co(C_2B_9H_{11})_2]$.

6. A compound as recited in claim 1, wherein at least one of the groups $R^1$, $R^2$, $R^3$ and $R^4$ is $(C_2B_9H_{11})$phenyl or $(C_2B_{10}H_{11})$phenyl.

7. A compound as recited in claim 1, wherein each of the groups $R^1$, $R^2$, $R^3$ and $R^4$ is $(C_2B_9H_{11})$phenyl or $(C_2B_{10}H_{11})$phenyl.

8. A compound as recited in claim 1, wherein at least one of the pairs of groups $Y^1$, $Y^2$, $Y^3$ and $Y^4$ is —CH=CH—CH=CH—, so that the compound contains a fused benzene ring at those positions.

9. A compound as recited in claim 1, wherein each of the pairs of groups $Y^1$, $Y^2$, $Y^3$ and $Y^4$ is —CH=CH—CH=CH—, so that the compound contains four fused benzene rings, one such fused benzene rings at each of those four positions.

10. A compound as recited in claim 1, wherein said compound is Compound 5 as depicted below:
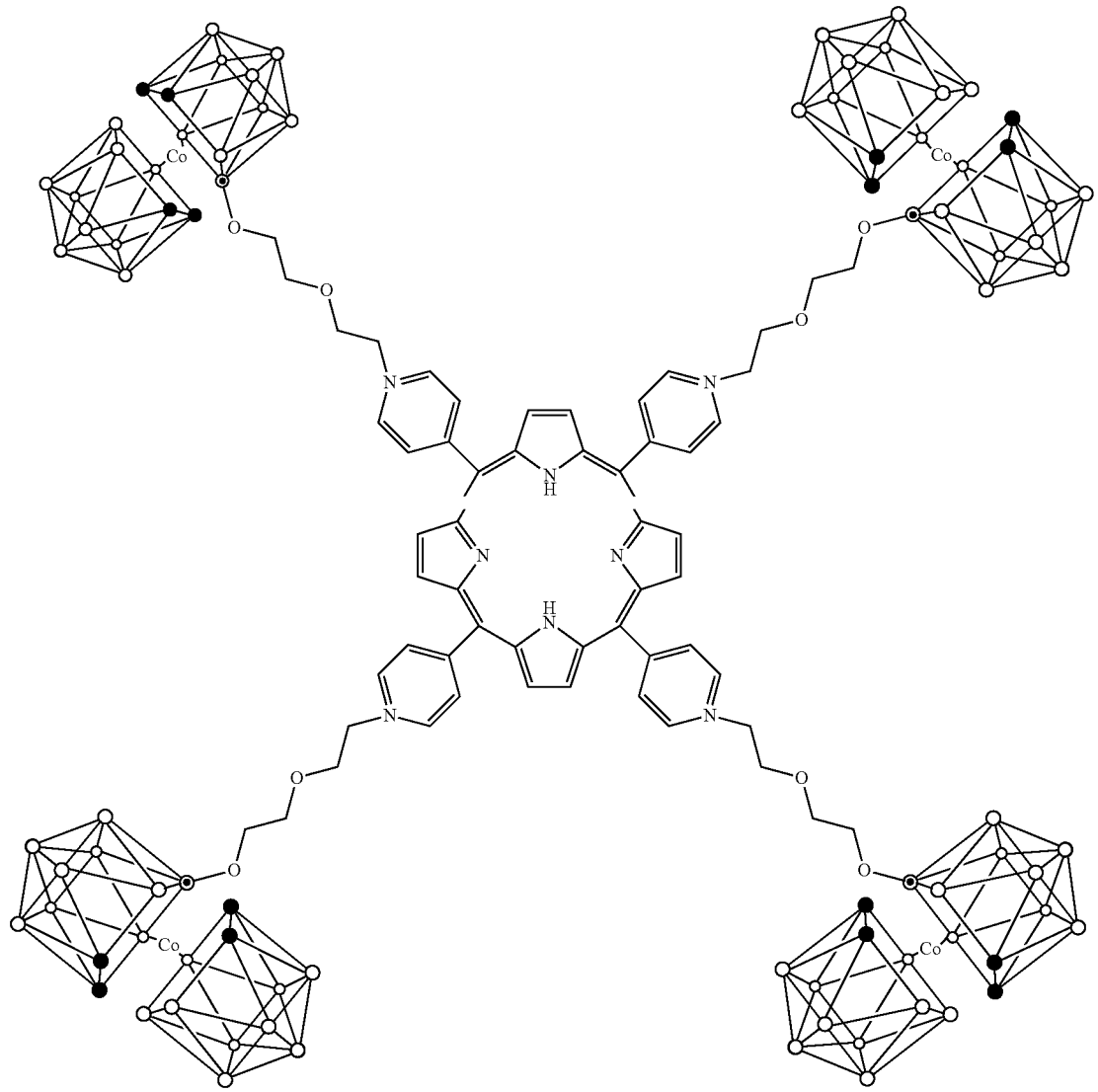
Compound 5

11. A compound as recited in claim 1, wherein said compound is Compound 13 as depicted below:
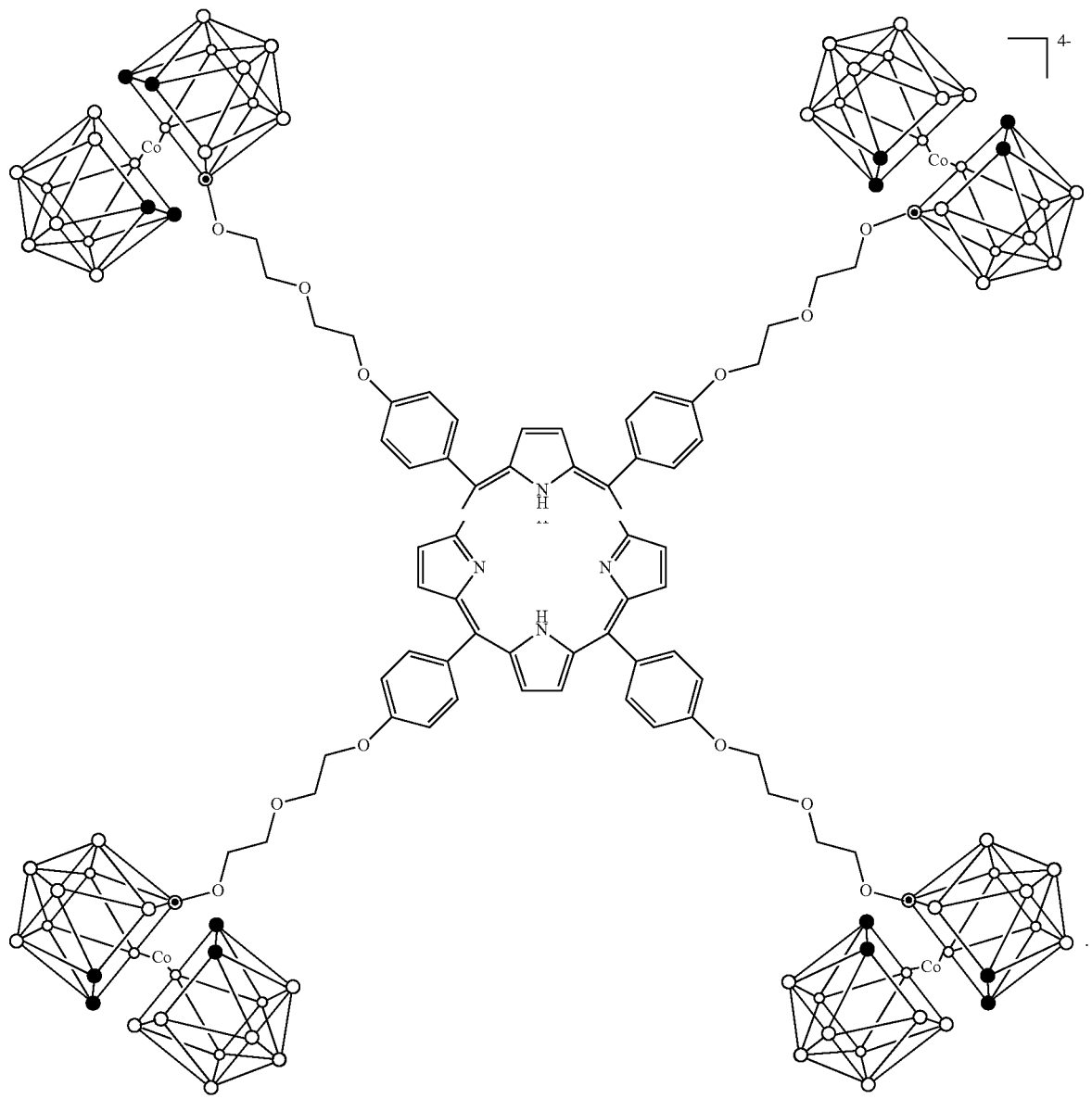
Compound 13

12. A compound as recited in claim 1, wherein said compound is Compound 19 as depicted below:
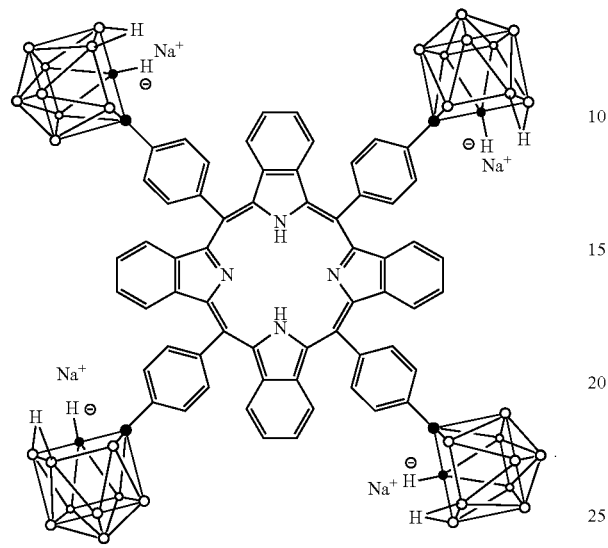
Compound 19
13. A compound as recited in claim 1, wherein said compound is Compound 25 as depicted below:
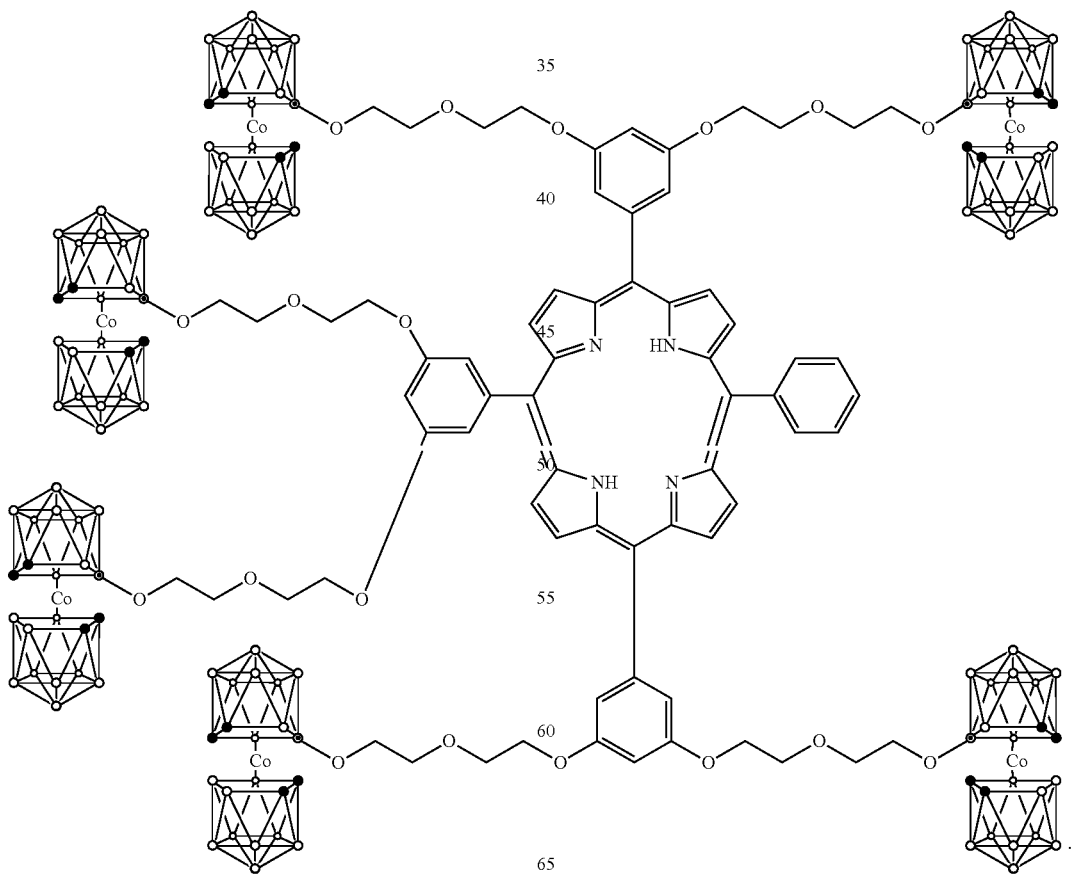
Compound 25

14. A compound as recited in claim 1, wherein said compound is Compound 31 as depicted below:
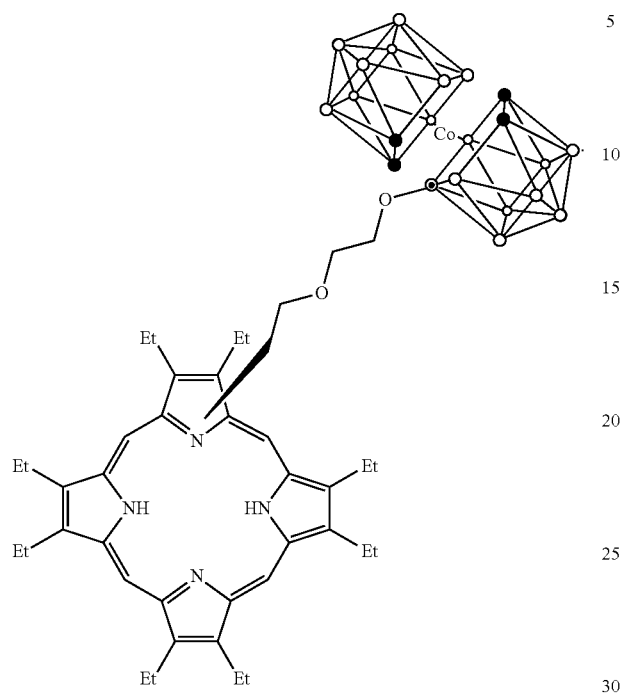
Compound 31
* * * * *